(12) United States Patent
Wada et al.

(10) Patent No.: US 11,278,369 B2
(45) Date of Patent: Mar. 22, 2022

(54) CONTROL DEVICE, CONTROL METHOD, AND SURGICAL SYSTEM

(71) Applicant: SONY CORPORATION, Tokyo (JP)

(72) Inventors: Seiji Wada, Kanagawa (JP); Takeshi Maeda, Tokyo (JP); Kana Matsuura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 490 days.

(21) Appl. No.: 16/092,235

(22) PCT Filed: Mar. 6, 2017

(86) PCT No.: PCT/JP2017/008830
§ 371 (c)(1),
(2) Date: Oct. 9, 2018

(87) PCT Pub. No.: WO2017/187795
PCT Pub. Date: Nov. 2, 2017

(65) Prior Publication Data
US 2019/0328479 A1 Oct. 31, 2019

(30) Foreign Application Priority Data
Apr. 28, 2016 (JP) .............................. JP2016-090167

(51) Int. Cl.
*A61B 90/25* (2016.01)
*A61B 34/37* (2016.01)
(Continued)

(52) U.S. Cl.
CPC .............. *A61B 90/25* (2016.02); *A61B 34/37* (2016.02); *A61B 90/50* (2016.02); *B25J 9/1676* (2013.01);
(Continued)

(58) Field of Classification Search
CPC ......... A61B 90/25; A61B 34/37; A61B 90/50; A61B 2090/373; A61B 2017/00203;
(Continued)

(56) References Cited

U.S. PATENT DOCUMENTS 7,084,867 B1 * 8/2006 Ho .......................... G06F 3/016
345/419
9,477,307 B2 * 10/2016 Chizeck ................. A61B 34/25
(Continued)

FOREIGN PATENT DOCUMENTS

JP 2004-223128 A 8/2004
JP 2005-14108 A 1/2005
(Continued)

OTHER PUBLICATIONS

International Search Report dated May 16, 2017, in PCT/JP2017/008830, filed Mar. 6, 2017.

*Primary Examiner* — Bhavesh V Amin
(74) *Attorney, Agent, or Firm* — Xsensus LLP

(57) ABSTRACT

To provide a control device, control method, and surgical system that can further improve safety. Provided is the control device including: a driving control unit (146) configured to control driving of an arm unit (112) that supports a medical instrument (111); a region setting unit (142) configured to set an intrusion appropriateness region for which appropriateness of intrusion of the medical instrument or the arm unit is determined in a space on a basis of a peripheral image showing a peripheral state of the medical instrument or the arm unit; an intrusion determination unit (144) configured to determine presence/absence of intrusion of the medical instrument or the arm unit into the intrusion appropriateness region when the driving control unit controls driving of the arm unit in accordance with a non-contact operation by a user with respect to the arm unit; and an action instruction unit (145) configured to cause an
(Continued)

intrusion hindering action for hindering intrusion of the medical instrument or the arm unit into the intrusion appropriateness region to be executed in accordance with a determination result of the intrusion determination unit.

17 Claims, 9 Drawing Sheets

(51) Int. Cl.
| | |
|---|---|
| *A61B 90/50* | (2016.01) |
| *B25J 9/16* | (2006.01) |
| *B25J 19/06* | (2006.01) |
| *G02B 21/00* | (2006.01) |
| *G02B 21/36* | (2006.01) |
| *A61B 90/00* | (2016.01) |
| *A61B 17/00* | (2006.01) |

(52) U.S. Cl.
CPC ............. *B25J 9/1689* (2013.01); *B25J 19/06* (2013.01); *G02B 21/0012* (2013.01); *G02B 21/36* (2013.01); *A61B 2017/00203* (2013.01); *A61B 2017/00207* (2013.01); *A61B 2017/00973* (2013.01); *A61B 2090/373* (2016.02)

(58) Field of Classification Search
CPC ........... A61B 2017/00207; A61B 2017/00973; A61B 2090/08021; A61B 2090/0811; A61B 2034/2055; A61B 2034/2065; A61B 34/30; A61B 34/74; A61B 34/35; B25J 9/1676; B25J 9/1689; B25J 19/06; B25J 3/00; G02B 21/0012; G02B 21/36; G05B 2219/45121
See application file for complete search history.

(56) References Cited

U.S. PATENT DOCUMENTS

| | | | | |
|---|---|---|---|---|
| 9,753,542 | B2* | 9/2017 | Chizeck | A61B 34/25 |
| 2003/0112281 | A1* | 6/2003 | Sriram | A63F 13/52 |
| | | | | 345/619 |
| 2005/0065658 | A1* | 3/2005 | Green | A61B 1/00193 |
| | | | | 700/245 |
| 2009/0278915 | A1* | 11/2009 | Kramer | B60K 37/06 |
| | | | | 348/48 |
| 2010/0063630 | A1* | 3/2010 | Sutherland | A61B 34/30 |
| | | | | 700/264 |
| 2011/0245844 | A1 | 10/2011 | Jinno | |
| 2014/0058406 | A1* | 2/2014 | Tsekos | F16C 1/20 |
| | | | | 606/130 |
| 2014/0276943 | A1 | 9/2014 | Bowling et al. | |
| 2014/0320392 | A1* | 10/2014 | Chizeck | G06F 3/016 |
| | | | | 345/156 |
| 2014/0320489 | A1* | 10/2014 | Chizeck | H04N 5/2256 |
| | | | | 345/420 |
| 2014/0320629 | A1* | 10/2014 | Chizeck | H04N 5/2256 |
| | | | | 348/81 |
| 2016/0030134 | A1* | 2/2016 | Shapter | A61B 34/25 |
| | | | | 606/130 |
| 2016/0154620 | A1 | 6/2016 | Tsuda et al. | |
| 2017/0024014 | A1* | 1/2017 | Chizeck | G06T 15/04 |
| 2017/0066131 | A1 | 3/2017 | Kamikawa et al. | |

FOREIGN PATENT DOCUMENTS

| | | | |
|---|---|---|---|
| JP | 2011-206312 | A | 10/2011 |
| JP | 2015-188566 | A | 11/2015 |
| JP | 2016-512084 | A | 4/2016 |
| WO | WO 2015/0129473 | A1 | 9/2015 |

* cited by examiner

CONTROL DEVICE, CONTROL METHOD, AND SURGICAL SYSTEM

TECHNICAL FIELD

The present disclosure relates to a control device, a control method, and a surgical system.

BACKGROUND ART

In recent years, support arm devices for supporting inspection and surgery have been used in the medical field. For example, a method in which an arm unit of a support arm device supports an observation instrument such as an endoscope or a microscope for enlarging and observing an operating site and a doctor performs inspection or surgery while viewing an image photographed by the observation instrument has been proposed. Alternatively, another method in which a treatment instrument such as a forceps or a retractor is provided at a tip of an arm unit and a support arm device is caused to support or operate the treatment instrument, which was performed manually in the past, has also be proposed. Note that an observation instrument, a treatment instrument, and the like provided at a tip of an arm unit of a support arm device will be collectively referred to as medical instruments in the following description. In addition, the support arm device having the tip of the arm unit at which such an observation instrument is provided will also be referred to as an observation device in the following description.

In addition, support systems targeting surgery using such support arm devices have been developed. For example, Patent Literature 1 discloses a support system for a surgical system which supports medical instruments with a manipulator to perform surgery by operating the manipulator. In the technology disclosed in Patent Literature 1, a user sets a region or a route in an operating site within which a medical instrument is allowed to operate on the basis of three-dimensional information of the operating site of a patient photographed with a magnetic resonance imaging (MRI) device. In addition, during surgery, a position of the medical instrument is sensed and a warning is issued in a case in which the medical instrument deviates from the set region or route. According to this technology, it is expected that a situation in which the medical instrument inadvertently comes in contact with a part of the body of the patient can be avoided and thus safer surgery can be realized.

In the technology disclosed in Patent Literature 1, however, the region or route is set on the basis of the three-dimensional information of the operating site of the patient photographed with the MRI device beforehand. Since there are cases in which an actual situation inside the body cavity of a patient at the time of surgery does not necessarily match three-dimensional information thereof based on information acquired before the surgery, in such a case, there is concern of no warning effectively working and safety not being satisfactorily secured in the technology disclosed in Patent Literature 1. In addition, in the technology disclosed in Patent Literature 1, only prevention of contact of the medical instrument supported by the manipulator (i.e., an arm unit) with the body of the patient is considered. On the other hand, in the actual field of surgery, contact of an arm unit with a nearby object (e.g., a drape of a patient, a mayo instrument stand (a surgical instrument table), medical staff, a surgical device, etc.) may also occur when the arm unit is moved through a user operation. When such contact occurs, it obstructs movement of the arm unit, which makes surgery difficult to execute smoothly. Therefore, in order to realize safer surgery, it is necessary to also consider contact of the arm unit with a nearby object.

Meanwhile, with respect to industrial multi-articulated robot devices used in product assembly, welding work, painting work performed in factories and the like, for example, technologies for avoiding interference of nearby obstacles with arm units have been developed. Patent Literature 2, for example, discloses a method of a multi-articulated robot device with an arm unit having redundant degrees of freedom to control driving of the arm unit such that interference can be avoided with a position and a posture of an end effector provided at a tip of the arm unit fixed. By applying the interference avoiding technology for industrial multi-articulated robot devices, like the technology disclosed in Patent Literature 2, to driving control of a medical support arm device, there is a possibility of realization of safer surgery.

CITATION LIST

Patent Literature

Patent Literature 1: JP 2004-223128A
Patent Literature 2: JP 2005-14108A

DISCLOSURE OF INVENTION

Technical Problem

Here, in the technology disclosed in Patent Literature 2, by controlling driving of an arm unit such that the distance between a comparison reference point set for an obstacle and a comparison target point set for a multi-articulated robot device has a maximum value, an operation of the arm unit to avoid interference is realized. With respect to an industrial multi-articulated robot device, for example, the same work is assumed to be repeated in flow work, and a positional relation between the multi-articulated robot device and an obstacle to be avoided is considered to rarely change, and thus it is considered that a certain effect can be exhibited even in driving control using such a comparison reference point and comparison target point set in advance.

Meanwhile, it is assumed with respect to a medical support arm device that a nearby object frequently moves during surgery. Thus, if the technology disclosed in Patent Literature 2 were applied without change, it would be considered difficult to effectively hinder interference of an arm unit with a nearby object.

A technology of controlling driving of an arm unit of a medical support arm device more safely has been demanded taking the above-described circumstances into consideration. Therefore, the present disclosure proposes a novel and improved control device, control method, and surgical system that can further improve safety.

Solution to Problem

According to the present disclosure, there is provided a control device including: a driving control unit configured to control driving of an arm unit that supports a medical instrument; a region setting unit configured to set an intrusion appropriateness region for which appropriateness of intrusion of the medical instrument or the arm unit is determined in a space on a basis of a peripheral image showing a peripheral state of the medical instrument or the arm unit; an intrusion determination unit configured to determine presence/absence of intrusion of the medical instrument or the arm unit into the intrusion appropriateness region when the driving control unit controls driving of the arm unit in accordance with a non-contact operation by a user with respect to the arm unit; and an action instruction unit configured to cause an intrusion hindering action for hindering intrusion of the medical instrument or the arm unit into the intrusion appropriateness region to be executed in accordance with a determination result of the intrusion determination unit.

In addition, according to the present disclosure, there is provided a control method including: setting, by a processor, an intrusion appropriateness region for which appropriateness of intrusion of a medical instrument or an arm unit supporting the medical instrument is determined in a space on a basis of a peripheral image showing a peripheral state of the medical instrument or the arm unit; determining presence/absence of intrusion of the medical instrument or the arm unit into the intrusion appropriateness region when driving of the arm unit is controlled in accordance with a non-contact operation by a user with respect to the arm unit; and causing an intrusion hindering action for hindering intrusion of the medical instrument or the arm unit into the intrusion appropriateness region to be executed in accordance with a determination result of the presence/absence of intrusion of the medical instrument or the arm unit into the intrusion appropriateness region.

In addition, according to the present disclosure, there is provided a surgical system including: a microscope unit configured to be supported by an arm unit and to enlarge and photograph an operating site; a display device configured to display an image of the operating site photographed by the microscope unit; a peripheral image acquisition camera configured to photograph a peripheral image showing a peripheral state of the microscope unit or the arm unit; a driving control unit configured to control driving of the arm unit; a region setting unit configured to set an intrusion appropriateness region for which appropriateness of intrusion of the microscope unit or the arm unit is determined in a space on a basis of the peripheral image photographed by the peripheral image acquisition camera; an intrusion determination unit configured to determine presence/absence of intrusion of the microscope unit or the arm unit into the intrusion appropriateness region when the driving control unit controls driving of the arm unit in accordance with a non-contact operation by a user with respect to the arm unit; and an action instruction unit configured to cause an intrusion hindering action for hindering intrusion of the microscope unit or the arm unit into the intrusion appropriateness region to be executed in accordance with a determination result of the intrusion determination unit.

According to the present disclosure, an intrusion appropriateness region is set on the basis of a peripheral image showing a peripheral state of a medical instrument or an arm unit. In addition, when driving of the arm unit is controlled in accordance with a non-contact operation by a user, the intrusion hindering action is executed in accordance with the presence/absence of intrusion of the medical instrument or the arm unit into the intrusion appropriateness region. Since the intrusion appropriateness region is set reflecting the actual peripheral state according to the configuration, the intrusion appropriateness region can be set more appropriately, and the intrusion hindering action can be executed more appropriately. Accordingly, safer driving control of the arm unit can be realized.

Advantageous Effects of Invention

Safety can be further improved according to the present disclosure described above. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
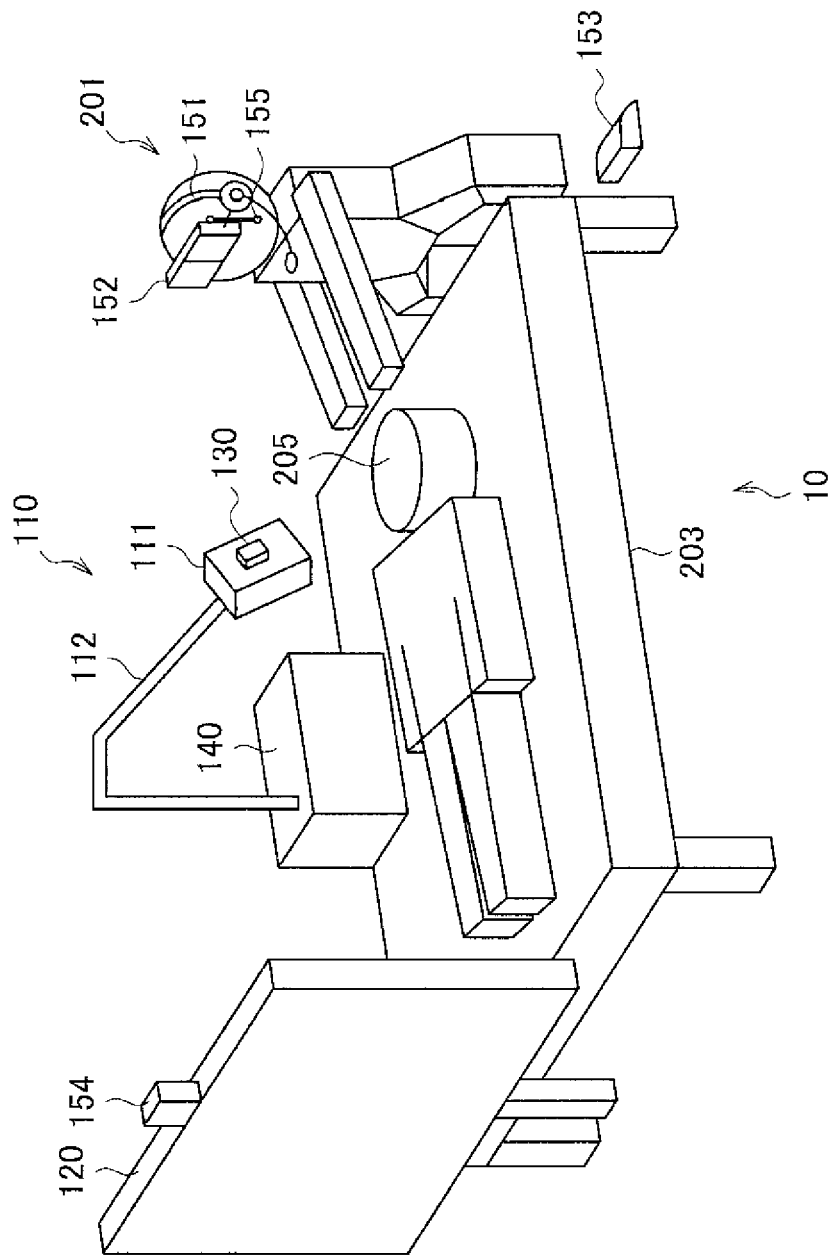
FIG. 1 is a diagram illustrating a schematic configuration of a surgical system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.

1. Configuration of surgical system
1-1. Schematic configuration
1-2. Functional configuration
2. Control method
3. Modified example
4. Configuration example of observation device
5. Supplement Note that, as an example of the present disclosure, an embodiment in which a support arm device is an observation device in which an electronic imaging microscope unit having a function of enlarging and photographing an operating site is provided at a tip of an arm unit thereof, and surgery (e.g., brain neurosurgery, ophthalmic surgery, cardiac surgery, etc.) is performed using the observation device will be described below. The present disclosure, however, is not limited thereto. The technology according to the present embodiment can be applied to all types of support arm devices, regardless of the type of medical instrument supported at the tip of the arm unit. In addition, medical practice to which the technology according to the present disclosure is applied is not limited to surgery, and can be various types of medical practice such as inspection. The technology according to the present disclosure realizes higher safety in driving control of a support arm device, and similar effects can be exhibited regardless of the type of medical instrument supported at the tip of the arm unit and details of medical practice to which the technology is applied.

In addition, in the following description, a user using a surgical system, which will be described below, and a user operating an observation device, which will be described below, will be referred to as operators for the sake of convenience. However, the description is not limited to a user using the surgical system and a user operating the observation device, and a subject using the observation system and the subject operating the observation device may be other medical staff such as an assistant, a nurse, and the like.

1. CONFIGURATION OF SURGICAL SYSTEM (1-1. Schematic Configuration)

A schematic configuration of a surgical system according to an exemplary embodiment of the present disclosure will be described with reference to FIG. 1. FIG. 1 is a diagram illustrating a schematic configuration of a surgical system according to the present embodiment. In FIG. 1, a state in which a surgeon 201 is performing surgery for a patient 205 lying on a patient bed 203 using the surgical system 10 according to the present embodiment is schematically illustrated.

Referring to FIG. 1, the surgical system 10 according to the present embodiment includes an observation device 110, a display device 120, a peripheral image acquisition camera 130, a control device 140, a microphone 151, an eyeglass-type wearable device 152, a foot switch 153, and an operation recognition camera 154. Note that, although it will be described below in detail, the microphone 151, the eyeglass-type wearable device 152, the foot switch 153, and the operation recognition camera 154 function as input devices for receiving operations of the surgeon 201 in a hands-free mode. Thus, the elements will also be collectively referred to as a hands-free input device in the following description.

(Observation Device)

The observation device 110 includes a microscope unit 111 and an arm unit 112 that supports the microscope unit 111 at a tip thereof. Note that, in FIG. 1, a simplified configuration of the observation device 110 is illustrated for the sake of simplicity. A specific configuration example of the observation device 110 will be described again in detail in (4. Configuration example of observation device) below.

The microscope unit 111 is configured with an image sensor, an optical system for guiding light from an observation target (observation light) to the image sensor, and the like accommodated in a housing. The image sensor generates a signal corresponding to the observation light, i.e., an image signal corresponding to an observation image, by receiving and photoelectrically converting the observation light. As described, the microscope unit 111 is an electronic imaging microscope unit that electronically photographs images. The microscope unit 111 transmits the acquired image signal to the control device 140.

The optical system of the microscope unit 111 has a focus lens for adjusting focal distances and a zoom lens for adjusting magnifications. In the microscope unit 111, a driving mechanism for moving the focus lens and the zoom lens in the optical axis direction is provided. When positions of the focus lens and the zoom lens are appropriately moved via the driving mechanism by control of the control device 140, a focal distance and a magnification of the microscope unit 111 are adjusted.

In addition, in the present embodiment, the microscope unit 111 is configured as a stereo camera having a pair of image sensors. That is, the microscope unit 111 acquires an image signal for 3D display.

The arm unit 112 is configured by connecting a plurality of links to each other by a plurality of joint units to be rotatable. Actuators are provided at each of the joint units, and by controlling driving of the actuators with control of the control device 140, an attitude of the arm unit and a position and an attitude of the microscope unit 111 are controlled. An attitude of the arm unit and a position and an attitude of the microscope unit 111 are appropriately adjusted so that the microscope unit 111 photographs an operating site through an operation by the surgeon 201 during surgery.

In the present embodiment, the arm unit 112 is configured to have a redundant degree of freedom. Here, having a redundant degree of freedom means having more degrees of freedom than the minimum degrees of freedom necessary for realizing a desired position and attitude of the microscope unit 111. For example, if the arm unit 112 is generally configured to have a total of six degrees of freedom of three translational degrees of freedom and three rotational degrees of freedom with respect to a motion of the microscope unit 111, positions and attitude of the microscope unit 111 can be freely controlled within an operable range of the arm unit 112. Thus, in the present embodiment, the arm unit 112 is configured to have more degrees of freedom than six degrees of freedom (e.g., seven degrees of freedom or eight degrees of freedom) with respect to motions of the microscope unit 111. Having a redundant degree of freedom, for example, the arm unit 112 can be driven so that only an attitude of the arm unit 112 is changed in a state in which a position and an attitude of the microscope unit 111 are locked.

(Display Device)

The display device 120 is disposed at a position facing the surgeon 201 having the patient bed 203 interposed therebetween. On the display device 120, an image of the operating site photographed by the microscope unit 111 of the observation device 110 by control of the control device 140 is projected. The surgeon 201 performs various kinds of treatment on the operating site while observing the operating site in the image projected on the display device 120.

In addition, as the display device 120, an eyeglass-type 3D display is used. Accordingly, the surgeon 201 can observe the operating site more precisely because stereoscopic viewing is possible. Note that a specific configuration of the display device 120 is not limited, and as the display device 120, various known display devices, for example, a liquid crystal display device, an electro-luminescence (EL) display device, or the like, may be applied.

In addition, instead of or along with the image of the operating site, the display device 120 may display various kinds of information relating to the surgery (e.g., physical data of the patient 205, the result of inspection performed beforehand, information of the surgical technique, etc.). Switching of the display may be executed in accordance with an arbitrary operation by the surgeon 201.

(Ambient Image Acquisition Camera)

The peripheral image acquisition camera 130 is provided in the microscope unit 111 of the observation device 110 and photographs peripheral images showing a state of surroundings of the microscope unit 111 and the arm unit 112. The peripheral image acquisition camera 130 is configured, for example, as a camera having a wide angle lens to photograph an image of as wide a range as possible. In addition, a plurality of peripheral image acquisition cameras 130 may be provided in the microscope unit 111 in order to obtain images of all surroundings. The peripheral image acquisition camera 130 transmits an image signal of a photographed peripheral image to the control device 140. Note that, although a peripheral image is defined as an "image showing a state around the microscope unit 111 'and' the arm unit 112" in the present embodiment for the sake of convenience, the present disclosure is not limited thereto. For example, a peripheral image may be an "image showing a state around the microscope unit 111 'or' the arm unit 112." A peripheral image may be set as an "image showing a state around the microscope unit 111 'and/or' the arm unit 112," and how to set a peripheral image at the time of implementation may be appropriately set by an operator, a designer of the surgical system 10, or the like.

Here, although it will be described below in detail, a peripheral image is used to display a peripheral image with distance information (an image in which information of a distance between the microscope unit 111 and the arm unit 112 and a peripheral object is added to the peripheral image) for setting an intrusion appropriateness region. Thus, as the peripheral image acquisition camera 130, one that can acquire distance information (e.g., a stereo camera, etc.) is used. The distance information acquired by the peripheral image acquisition camera 130 is also transmitted to the control device 140 along with the image signal.

(Control Device)

The control device 140 comprehensively controls operations of the surgical system 10. Specifically, the control device 140 controls driving of the arm unit 112 in accordance with an operation of the surgeon 201 to control a position and an attitude of the microscope unit 111 (i.e., a photographing range and a photographing direction). In addition, the control device 140 controls photographing conditions (a focal distance, a magnification, and the like) of the microscope unit 111 in accordance with an operation of the surgeon 201. In addition, the control device 140 controls display of the display device 120.

Here, driving mechanisms of motors and the like, encoders for detecting rotation angles of each of the joint units and the like are mounted in the actuators provided at each of the joint units of the arm unit 112. Detection values of the encoders are frequently transmitted to the control device 140, and the control device 140 can perform driving control of the arm unit 112 using the detection values of the encoders. Specifically, the control device 140 can ascertain a current state of the arm unit 112 (specifically, a current state of the arm unit 112, and a current position and attitude of the microscope unit 111) on the basis of information of rotational angles of each of the joint units detected by the encoders and an internal model of the arm unit 112 input to the control device 140 beforehand (which is a control model used in driving control of the arm unit 112 and a model including geometric information of the arm unit 112 to be controlled and information regarding movement of the arm unit 112). Using the ascertained information, the control device 140 calculates a control value with respect to each joint unit that is likely to realize movement of the microscope unit 111 in accordance with an operation of the surgeon 201 (e.g., a rotational angle in a case of position control, generated torque in a case of force control, etc.) and drives driving mechanisms of each joint unit in accordance with the control value. Accordingly, driving control of the arm unit 112 in accordance with the operation of the surgeon 201 can be realized.

In addition, the control device 140 sets an operation mode of the arm unit 112. Here, the operation mode is an operation mode of the arm unit 112 in accordance with the type of operation by the surgeon 201 when the control device 140 performs driving control of the arm unit 112. Specifically, the operation mode includes a manual mode and a hands-free mode.

The manual mode is an operation mode in which the surgeon 201 brings his or her hand in direct contact with the microscope unit 111 and the arm unit 112 and driving of the arm unit 112 is controlled in accordance with an operation of moving the arm unit 112 while force is exerted on the arm unit 112. An operation performed in the manual mode will also be referred to as a direct operation in the following description for the sake of convenience. In the manual mode, for example, the control device 140 drives the arm unit 112 through force control. At this time, the control device 140 can perform so-called power assist control in which an external force from the surgeon 201 is received and the actuators of each of the joint units are driven so that the arm unit 112 is smoothly moved with the external force. Since driving of the arm unit 112 is controlled so that a direct operation of the surgeon 201 is supported in power assist control, it is possible to give a light operation feeling to the surgeon 201 as if the operator were moving the arm unit 112 under zero gravity, and thus operability for the surgeon 201 can be improved.

On the other hand, the hands-free mode is an operation mode in which driving of the arm unit 112 is controlled in accordance with an operation performed by the surgeon 201 without using his or her hands. An operation performed in the hands-free mode will also be referred to as a hands-free operation in the following description for the sake of convenience. Specifically, hands-free operations include operations using a voice, a line of sight, a motion of the head (a so-called head track), a gesture, and a leg via the foot switch 153 in the present embodiment. In the hands-free mode, for example, the control device 140 drives the arm unit 112 so that the microscope unit 111 is moved by a movement amount designated by the surgeon 201 using a hands-free operation in position control.

The surgeon 201 holds treatment instruments with both hands during surgery, and thus since the operator can perform driving control of the arm unit 112 without using his or her hands in the hands-free mode, it is not necessary for the surgeon 201 to release the treatment instruments once to operate the microscope unit 111. In addition, since the operator can perform driving control of the arm unit 112 without using his or her hands in the hands-free mode, it is not necessary for the surgeon 201 to touch an input device or the like placed in an unsanitary area with his or her hands to operate the microscope unit 111. By operating the arm unit 112 in the hands-free mode as described above, surgery can be performed more smoothly.

Note that switching of the operation mode may be performed through arbitrary input of an instruction by the surgeon 201 (e.g., input of an instruction via a hands-free input device, or input of an instruction via another input device such as a switch).

In addition, the control device 140 sets a region for which appropriateness of intrusion of the microscope unit 111 and the arm unit 112 into a space is determined (which will also be referred to as an intrusion appropriateness region below) on the basis of a peripheral image photographed by the peripheral image acquisition camera 130 at the time of driving control of the arm unit 112. In addition, in a case in which the microscope unit 111 and the arm unit 112 intrude into the intrusion appropriateness region while the arm unit 112 is driven in accordance with the hands-free operation by the surgeon 201, the control device 140 causes an action for hindering intrusion of the arm unit 112 into the intrusion appropriateness region (which will also be referred to as an intrusion hindering action below), for example, stopping an operation of the arm unit 112 and/or outputting a warning, to be executed. Note that specific functions of the control device 140 will be described again in detail in (1-2. Functional configuration) below. Note that, although the intrusion appropriateness region (specifically, an intrusion prohibited region, an intrusion attention region, and an intrusion allowed region which will be described below) is set as a "region for which appropriateness of intrusion of the microscope unit 111 'and' the arm unit 112 is determined" in the present embodiment for the sake of convenience, the present disclosure is not limited thereto. For example, an intrusion appropriateness region may be a "region for which appropriateness of intrusion of the microscope unit 111 'or' the arm unit 112 is determined." An intrusion appropriateness region may be set as a "region for which appropriateness of intrusion of the microscope unit 111 'and/or' the arm unit 112 is determined," and how to set an intrusion appropriateness region at the time of implementation may be appropriately set by an operator, a designer of the surgical system 10, or the like.

Note that the control device 140 can be, for example, a processor such as a central processing unit (CPU), a graphics processing unit (GPU), or the like, a control board on which memory elements such as processors and memories are mixed, a general information processing device such as a personal computer (PC), or the like. When a processor included in the control device 140 executes an arithmetic operation process in accordance with a predetermined program, each of the above-described functions can be realized.

(Hands-Free Input Device)

A hands-free input device is a generic name of input devices for receiving hands-free operations by the surgeon 201. Specifically, as the hands-free input device, the microphone 151, the eyeglass-type wearable device 152, the foot switch 153, and the operation recognition camera 154 are provided in the present embodiment.

The microphone 151 and the eyeglass-type wearable device 152 are worn by the surgeon 201. The microphone 151 collects a voice of the surgeon 201 and transmits a voice signal of the voice to the control device 140. The control device 140 receives the voice signal transmitted from the microphone 151, then performs a voice recognition process, and thereby recognizes the operation via the voice of the surgeon 201.

A line-of-sight detection sensor that detects a line of sight of the surgeon 201 is mounted in the eyeglass-type wearable device 152. The line-of-sight detection sensor of the eyeglass-type wearable device 152 transmits the detection result of the line of sight of the surgeon 201 to the control device 140. By analyzing the detection result, the control device 140 recognizes the operation via the line of sight of the surgeon 201. Note that the eyeglass-type wearable device 152 also has the function of 3D eyeglasses for viewing a 3D display on the display device 120.

The foot switch 153 transmits an operation signal indicating the content of the operation by a leg of the surgeon 201 to the control device 140. The control device 140 recognizes the operation by the surgeon 201 via the foot switch 153 on the basis of the operation signal.

The operation recognition camera 154 is disposed at a position at which an appearance of the surgeon 201 can be photographed. In the illustrated example, the operation recognition camera 154 is provided on the top of the display device 120 provided to face the surgeon 201. The operation recognition camera 154 transmits an image signal of the photographed image of the surgeon 201 to the control device 140. By performing an image recognition process on the basis of the image signal, the control device 140 detects a head track and a gesture of the surgeon 201 and recognizes the operation via the operation recognition camera 154. Note that a marker 155 is installed on the head of the surgeon 201, and the control device 140 detects movement of the marker 155 in an image of the surgeon 201 photographed by the operation recognition camera 154 and thus can recognize the direction and movement amount of the head track of surgeon 201.

The control device 140 performs the above-described control of a position and an attitude of the microscope unit 111, control of a photographing condition of the microscope unit 111, and control of display of the display device 120 on the basis of the operation by the surgeon 201 via the hands-free input device. Note that specific control to be performed in accordance with an operation can be arbitrarily set. For example, in a case in which an instruction with the concept of "direction" is included in an operation of the surgeon 201 for control of a position and an attitude of the microscope unit 111, the arm unit 112 can be driven so that the microscope unit 111 is moved in accordance with the instruction with the concept of "direction." In addition, in a case in which an instruction includes the concept of "inclination," for example, the arm unit 112 can be driven so that the microscope unit 111 changes its attitude in accordance with the instruction with the concept of "inclination."

The schematic configuration of the surgical system 10 according to the present embodiment has been described above. Note that a configuration of the surgical system 10 is not limited to the above-described configuration example. In the surgical system 10, for example, the microscope unit 111 of the observation device 110 may be configured as a stereo camera, or configured to have, for example, a single-plate image sensor to acquire an image signal for 2D display. In this case, a display device that supports 2D display is used as the display device 120, and thus the display device 120 two-dimensionally displays an image of an operating site. In addition, in the surgical system 10, for example, the arm unit 112 of the observation device 110 may not be configured to have a redundant degree of freedom with respect to motions of the microscope unit 111. For example, the arm unit 112 may be configured to have an arbitrary number of degrees of freedom equal to or fewer than six degrees of freedom. However, since there can be a desire for photographing an operating site in various directions during surgery, it is preferable for the arm unit 112 to have at least six degrees of freedom to freely move the microscope unit 111.

In addition, although the peripheral image acquisition camera 130 is mounted in the microscope unit 111 in the above-described configuration example, the present embodiment is not limited thereto. The peripheral image acquisition camera 130 may be installed at an arbitrary position as long as it can acquire peripheral images of the microscope unit 111 and the arm unit 112. The peripheral image acquisition camera 130 may be, for example, a so-called operating room camera provided on a ceiling of an operating room.

In addition, a type of hands-free input device is not limited to the above-described examples. The hands-free input device may be a device with which the surgeon 201 can input an operation without using his or her hands, and an arbitrary device may be applied as the hands-free input device.

(1-2. Functional Configuration)

Figure 2:
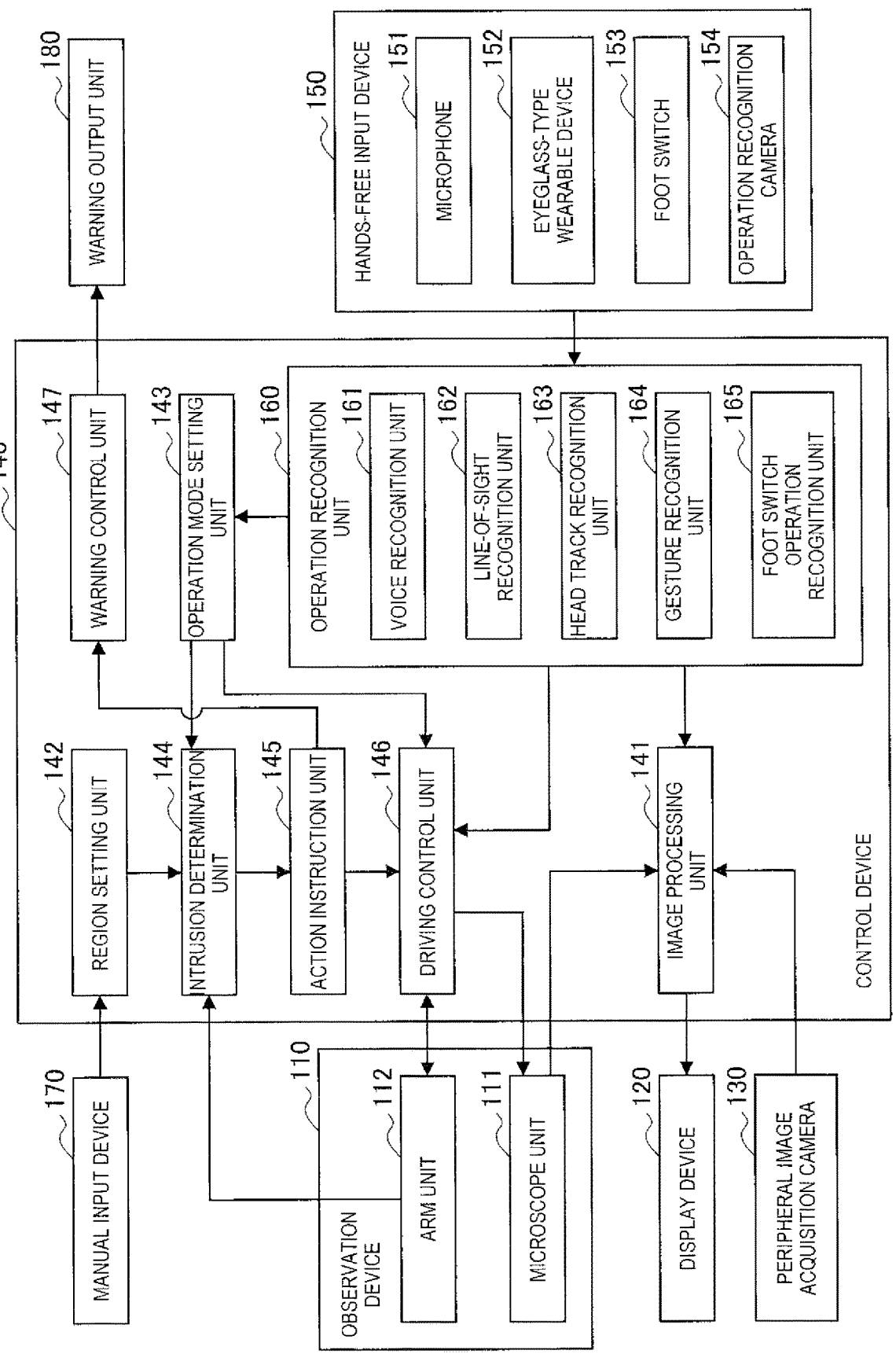
FIG. 2 is a block diagram illustrating an example of a functional configuration of a surgical system according to the present embodiment.

A functional configuration of the surgical system 10 illustrated in FIG. 1 will be described with reference to FIG. 2. FIG. 2 is a block diagram illustrating an example of a functional configuration of the surgical system 100 according to the present embodiment.

In FIG. 2, each of devices constituting the surgical system 10 illustrated in FIG. 1 (the microscope unit 111 and the arm unit 112 of the observation device 110, the display device 120, the peripheral image acquisition camera 130, the control device 140, and the hands-free input device 150), and each of the functions of the surgical system 10 are schematically illustrated by blocks. Since configurations and functions of the observation device 110, the display device 120, the peripheral image acquisition camera 130, and the hands-free input device 150 have already been described with reference to FIG. 1, functions of the control device 140 will be described here in detail.

Note that, although description and illustration are omitted in FIG. 1, the surgical system 10 further includes a manual input device 170 and a warning output unit 180 as illustrated in FIG. 2. The manual input device 170 is an input device other than the hands-free input device 150, and is an input device that the surgeon 201 touches with his or her hand to perform operation input. The manual input device 170 is, for example, a touch panel, a lever, a switch, and the like. In addition, the warning output unit 180 has a function of outputting a visual, auditory, and/or tactile warning to the surgeon 201. For example, the warning output unit 180 is configured as a lamp, a buzzer, and/or a vibration device installed on the surgeon 201, or the like. The vibration device may be, for example, provided in the eyeglass-type wearable device 152 or provided as an individual device. Alternatively, the warning output unit 180 may be configured by an arbitrary display device including the display device 120 and display light, letters, and the like indicating a warning on the display device. In the present embodiment, a device constituting the warning output unit 180 may be arbitrary, and an aspect of the warning may also be arbitrary.

The control device 140 has an operation recognition unit 160, an image processing unit 141, a region setting unit 142, an operation mode setting unit 143, an intrusion determination unit 144, an action instruction unit 145, a driving control unit 146, and a warning control unit 147 as its functions as illustrated.

(Process Before Treatment)

First, functions relating to a process executed before the surgeon 201 performs various kinds of treatment on an operating site after surgical settings are completed will be described. Note that the surgical settings can be, specifically, carrying the patient 205 into the operating room, work for exposing the operating site (cranioclasty in a case of brain neurosurgery), disposition of medical staff and surgical apparatuses, and the like.

Before the surgeon 201 performs treatment after the surgical settings are completed, the image processing unit 141 performs various kinds of image processing for displaying an image of the operating site on the display device 120 on an image signal of a peripheral image acquired by the peripheral image acquisition camera 130. Then, the processed image signal is transmitted to the display device 120 and the peripheral image is displayed on the display device 120 on the basis of the image signal. Note that, in the above-described image processing, for example, various kinds of known signal processing such as a development process (demosaicing process), a high image quality process (a band emphasis process, a super resolution process, a noise reduction (NR) process, and/or a camera shake correction process) and/or an enlargement process (i.e., an electronic zoom process) may be performed.

Figure 3:
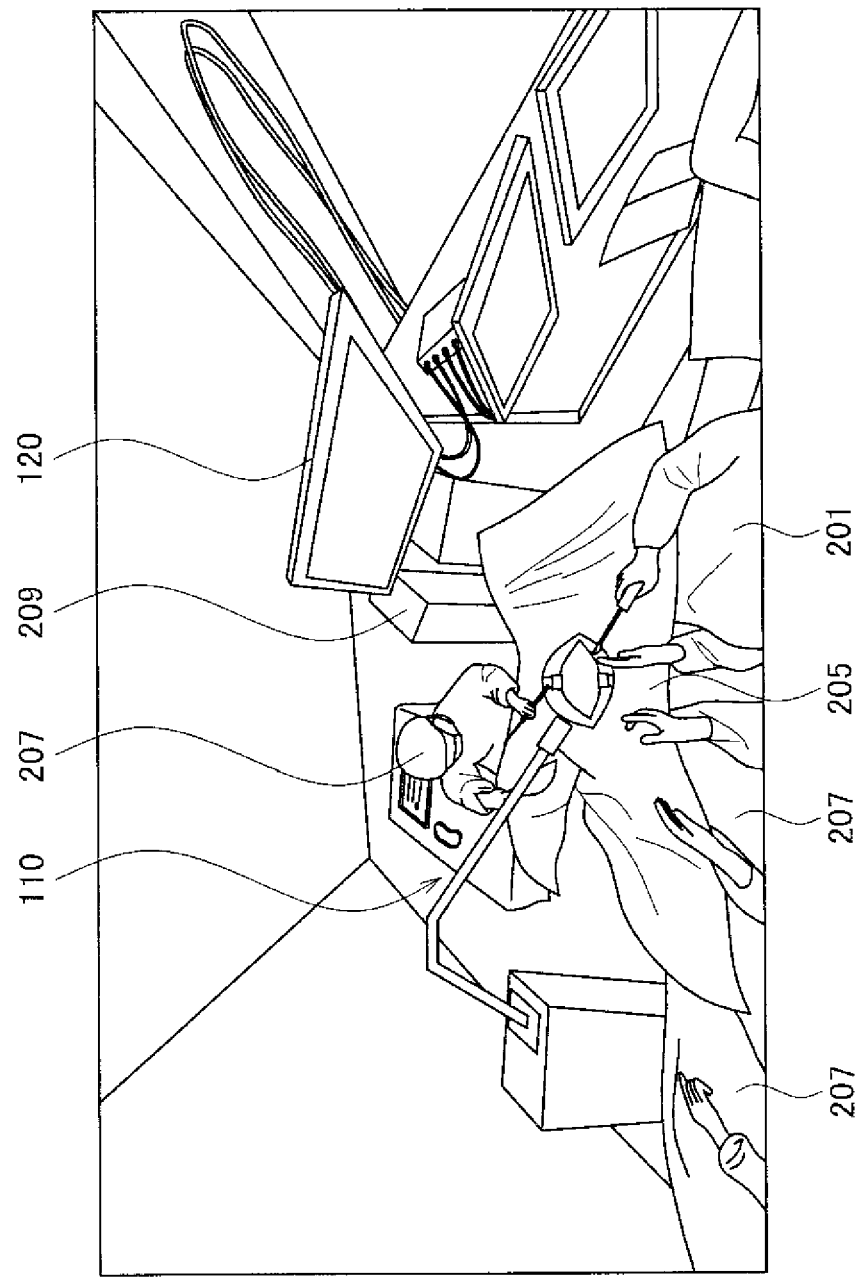
FIG. 3 is a diagram illustrating an example of a peripheral image acquired by a peripheral image acquisition camera.

FIG. 3 is a diagram illustrating an example of a peripheral image acquired by the peripheral image acquisition camera 130. As illustrated in FIG. 3, the peripheral image can include the microscope unit 111 and the arm unit 112 and nearby objects. In the illustrated example, the surgeon 201, other medical staff members 207, the patient 205, the display device 120, various surgical apparatuses 209, and the like are projected as nearby objects. Note that, in FIG. 3 and FIGS. 4 and 5, which will be described below, images that can be acquired in a case in which the peripheral image acquisition camera 130 is installed on a ceiling of the operating room are illustrated as examples.

In addition, the image processing unit 141 analyzes distances between the microscope unit 111 and the arm unit 112 and the nearby objects (e.g., the surgeon 201, the patient 205, other medical staff members 207, various surgical apparatuses 209, and the like) on the basis of the peripheral image, and causes a peripheral image with distance information obtained by adding the distance information to the peripheral image to be displayed on the display device 120.

Figure 4:
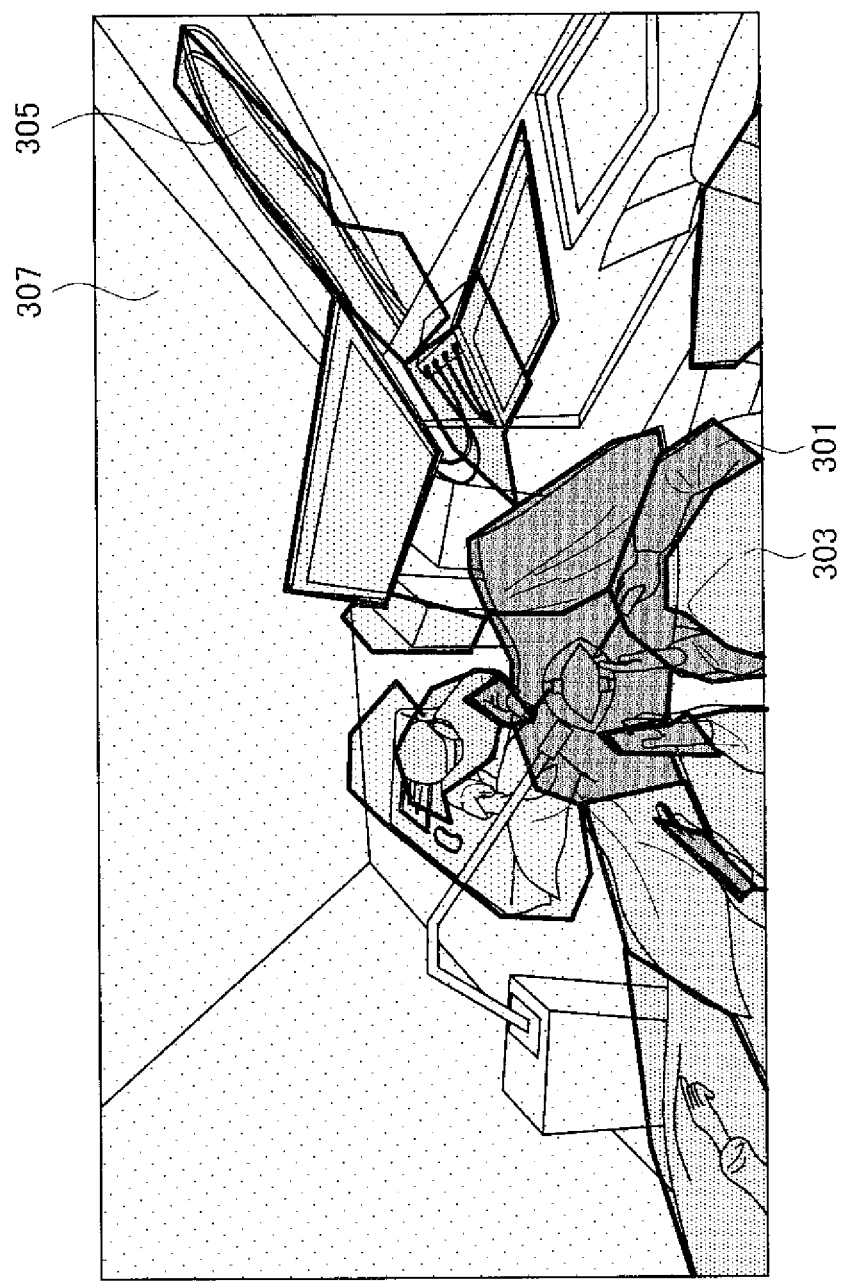
FIG. 4 is a diagram illustrating an example of a peripheral image with distance information.

FIG. 4 is a diagram illustrating an example of a peripheral image with distance information. As illustrated in FIG. 4, distance information is expressed by, for example, classifies the distances between the microscope unit 111 and the arm unit 112 and the nearby objects into several stages, divides the peripheral image into regions in accordance with the classification, and giving different colors to the regions for the stages. In the illustrated example, the peripheral image is divided into four regions including a region 301 in which objects in a very close distance from the microscope unit 111 and the arm unit 112 are present, a region 303 in which objects in a close distance from the microscope unit 111 and the arm unit 112 are present, a region 305 in which objects in a medium distance from the microscope unit 111 and the arm unit 112 are present, and a region 307 in which objects in a remote distance from the microscope unit 111 and the arm unit 112 are present, different colors are given to each of the regions 301 to 307, and thereby the distance information is expressed. Among these regions, the regions 301 to 305 are regions in the movable range of the arm unit 112, that is, regions to which the microscope unit 111 and the arm unit 112 are likely to intrude during driving, and the region 307 is a region out of the movable range of the arm unit 112.

Furthermore, the image processing unit 141 causes a display of a graphical user interface (GUI) for setting an intrusion appropriateness region to be displayed on the display device 120 on the basis of the peripheral image with distance information. Details of the GUI will be described below with reference to FIG. 5.

The region setting unit 142 sets an intrusion appropriateness region in a space on the basis of the peripheral image. In the present embodiment, the region setting unit 142 sets the intrusion appropriateness region in the space in accordance with a region selection operation performed by the surgeon 201 via the GUI for setting the intrusion appropriateness region.

Figure 5:
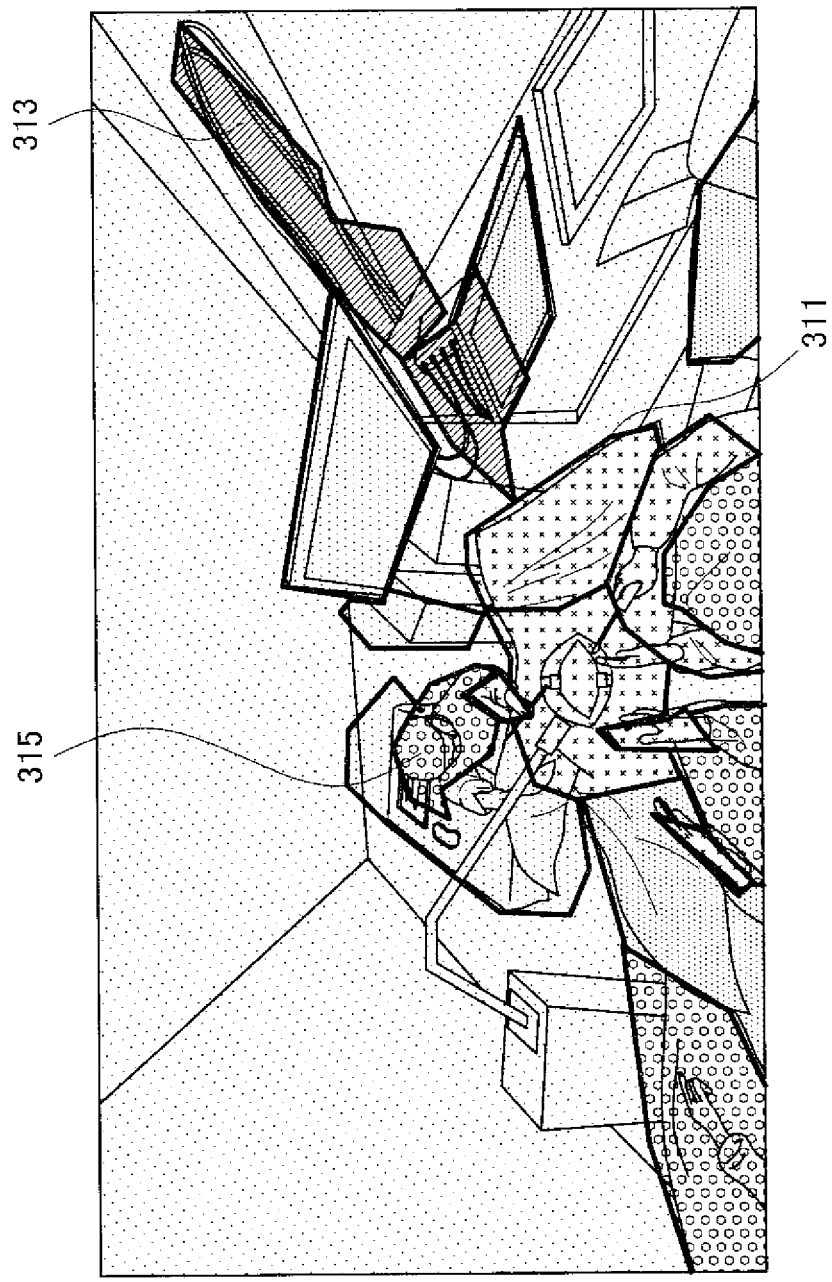
FIG. 5 is a diagram for describing an example of a GUI for setting an intrusion appropriateness region.

FIG. 5 is a diagram for describing an example of the GUI for setting an intrusion appropriateness region. The peripheral image with distance information is displayed on the GUI for setting an intrusion appropriateness region on the display device 120 as illustrated. By the surgeon 201 appropriately selecting each of the regions 301 to 307 classified in accordance with distances from the microscope unit 111 and the arm unit 112 in the peripheral image with distance information via the manual input device 170 on the GUI, an intrusion appropriateness region can be set for each of the regions. At that time, in a case in which there is each of the plurality of regions 301 to 307, an intrusion appropriateness region can be set for each of the regions. In a case in which the manual input device 170 is a touch panel, for example, the touch panel can be configured integrally with the display device 120, and the surgeon 201 can select a region to be set as an intrusion appropriateness region by bringing his or her finger, a stylus, or the like in direct contact with the regions 301 to 307 on the display screen. Alternatively, the manual input device 170 may be a pointing device such as a mouse, and the surgeon 201 may select a region to be set as an intrusion appropriateness region from the regions 301 to 307 by operating the pointer of the pointing device on the display screen.

Here, three types of regions, that is, an intrusion prohibited region 311, an intrusion attention region 313, and an intrusion allowed region 315 are set as intrusion appropriateness region in the present embodiment. The intrusion prohibited region 311 is a region within the movable range of the arm unit 112 and a region into which the microscope unit 111 and the arm unit 112 are prohibited from intruding in terms of safety. For example, the surgeon 201 selects a region in which an object that the microscope unit 111 and the arm unit 112 are prohibited from contact, such as the patient 205 and surgical apparatuses, is present as the intrusion prohibited region 311 from the regions 301 to 305 belonging to the movable range of the arm unit 112 on the GUI as illustrated.

The intrusion attention region 313 is a region in the movable range of the arm unit 112 and a region into which partial intrusion of the microscope unit 111 and the arm unit 112 causes no problem while attention should be paid thereto. For example, the surgeon 201 selects a region in which an object that is flexibly deformable even when being in contact with the microscope unit 111 and the arm unit 112, for example, a cable, a cloth, or the like suspended in the operating room, is present as the intrusion attention region 313 from the regions 301 to 305 belonging to the movable range of the arm unit 112 on the GUI as illustrated.

The intrusion allowed region 315 is a region in the movable range of the arm unit 112 and a region into which intrusion of the microscope unit 111 and the arm unit 112 causes no problem even though objects are present in the current situation. For example, the surgeon 201 selects a region in which an object that can avoid approach of the microscope unit 111 and the arm unit 112, for example, medical staff members (assistants, nurses, and the like), is present as the intrusion allowed region 315 from the regions 301 to 305 belonging to the movable range of the arm unit 112 on the GUI as illustrated.

The region setting unit 142 sets the intrusion prohibited region, the intrusion prohibition attention region, and the intrusion allowed region in the space in accordance with selection operations by the surgeon 201. Then, the region setting unit 142 provides information of the set intrusion prohibited region, intrusion prohibition attention region, and intrusion allowed region to the intrusion determination unit 144. Note that all the intrusion prohibited region, intrusion prohibition attention region, and intrusion allowed region may not be necessarily set, and at least one of the regions may be set.

As described above, the region setting unit 142 sets the intrusion appropriateness regions on the basis of the peripheral image photographed at the timing before the operator starts treatment after the surgical setting is completed in the present embodiment. Since the peripheral image acquired in that stage is an image reflecting the actual situation of the treatment, by setting the intrusion appropriateness region on the basis of the peripheral image, appropriate intrusion appropriateness region in accordance with the actual situation can be set. In addition, the intrusion appropriateness region can be arbitrarily set by the surgeon 201. By the surgeon 201 having full knowledge of the actual surgery site and setting the intrusion appropriateness regions, the intrusion appropriateness regions can be set more appropriately.

(Process During Treatment)

Next, functions relating to a process executed while the surgeon 201 is performing various kinds of treatment on an operating site after the intrusion appropriateness region setting process is performed will be described.

The operation recognition unit 160 recognizes an operation of the surgeon 201 on the basis of information indicating the operation of the surgeon 201 transmitted from the hands-free input device 150. Specifically, the operation recognition unit 160 has a voice recognition unit 161, a line-of-sight recognition unit 162, a head track recognition unit 163, a gesture recognition unit 164, and a foot switch operation recognition unit 165 as its functions.

The voice recognition unit 161 analyzes a voice signal of a voice of the surgeon 201 collected by the microphone 151 and thus recognizes an operation via the voice by the surgeon 201. The line-of-sight recognition unit 162 recognizes an operation by the surgeon 201 via a line of sight on the basis of the detection result of the line of sight of the surgeon 201 detected by the line-of-sight detection sensor mounted in the eyeglass-type wearable device 152. The head track recognition unit 163 and the gesture recognition unit 164 analyze an image of the surgeon 201 photographed by the operation recognition camera 154, and thereby recognize an operation via a head track and a gesture by the surgeon 201. The foot switch operation recognition unit 165 recognizes an operation via the foot switch 153 by the surgeon 201 on the basis of an operation signal of the operation by a leg of the surgeon 201 acquired by the foot switch 153.

The operations recognized by the operation recognition unit 160 include an operation relating to a change of the operation mode, an operation relating to an operation of the arm unit 112, and an operation relating to display control of the display device 120. In the case in which the recognized operation relates to a change of the operation mode, the operation recognition unit 160 provides information regarding details of the operation to the operation mode setting unit 143. In addition, in the case in which the recognized operation relates to an operation of the arm unit 112, the operation recognition unit 160 provides information regarding details of the operation to the driving control unit 146. In addition, in the case in which the recognized operation relates to display control of the display device 120, the operation recognition unit 160 provides information regarding details of the operation to the image processing unit 141.

The image processing unit 141 performs various kinds of image processing (e.g., similar processing to the above-described image processing for the peripheral image) for causing the image of the operating site acquired by the microscope unit 111 to be displayed on the display device 120 with respect to the image signal of the image of the operating site. Then, the image signal that has undergone the image processing is transmitted to the display device 120, and the display device 120 is caused to display the image of the operating site on the basis of the image signal. In addition, the image processing unit 141 may cause the display device 120 to display various kinds of information regarding the surgery in accordance with an operation by the surgeon 201, instead of or along with the image of the operating site.

The operation mode setting unit 143 sets the operation mode of the arm unit 112 to one of the manual mode and the hands-free mode in accordance with information regarding details of an operation of the surgeon 201 provided from the operation recognition unit 160. The operation mode setting unit 143 provides information regarding the set operation mode to the intrusion determination unit 144 and the driving control unit 146.

The intrusion determination unit 144 determines whether the microscope unit 111 and the arm unit 112 have intruded into an intrusion appropriateness region while driving of the arm unit 112 is controlled in accordance with a hands-free operation on the basis of information regarding the operation mode set by the operation mode setting unit 143, information regarding the intrusion appropriateness regions (i.e., the intrusion prohibited region, the intrusion prohibition attention region, and the intrusion allowed region) set by the region setting unit 142, and information indicating a state of the arm unit 112 transmitted from the arm unit 112 (specifically, a detection value of the encoder provided at each joint unit). Here, detection values of the encoders provided at each of the joint units of the arm unit 112 are frequently transmitted to the control device 140 as described above. The intrusion determination unit 144 can ascertain a current state of the arm unit 112 (specifically, an attitude of the arm unit 112, and a position and an attitude of the microscope unit 111) on the basis of the detection values of the encoders and the internal model of the arm unit 112 input to the control device 140 beforehand. Then, the intrusion determination unit 144 compares the ascertained current state of the arm unit 112 with the intrusion appropriateness regions set in the space, and thereby determines the presence/absence of intrusion of the microscope unit 111 and the arm unit 112 into the intrusion appropriateness regions.

Note that, although "the intrusion determination unit 144 determines whether the microscope unit 111 and the arm unit 112 have intruded into the intrusion appropriateness regions" is described in the present specification for the sake of convenience, actually, the intrusion determination unit 144 may determine that the microscope unit 111 and the arm unit 112 have intruded into the intrusion appropriateness regions in a case in which the microscope unit 111 and the arm unit 112 are about to intrude into the intrusion appropriateness regions. For example, the intrusion determination unit 144 determines that the microscope unit 111 and the arm unit 112 have intruded into the intrusion appropriateness regions in a case in which distances between the microscope unit 111 and the arm unit 112 and the intrusion appropriateness regions are equal to or shorter than a predetermined threshold value. Accordingly, before the microscope unit 111 and the arm unit 112 actually intrude into the intrusion appropriateness regions, an intrusion hindering action is executed with an instruction from the action instruction unit 145, which will be described below, and thus intrusion of the microscope unit 111 and the arm unit 112 into the intrusion appropriateness regions can be prevented in advance.

The intrusion determination unit 144 provides information regarding the determination result to the action instruction unit 145. Note that the intrusion determination unit 144 does not perform the intrusion presence/absence determination process in a case in which driving of the arm unit 112 is controlled in the manual mode in accordance with a direct operation by the surgeon 201. The reason for this will be described below.

The action instruction unit 145 issues an instruction to perform an intrusion hindering action on the basis of the determination result by the intrusion determination unit 144. In the present embodiment, the action instruction unit 145 issues instructions with respect to different intrusion hindering actions to the driving control unit 146 and/or the warning control unit 147 in accordance with aspects of intrusion of the microscope unit 111 and the arm unit 112 into the intrusion appropriateness regions.

Specifically, in a case in which the microscope unit 111 and the arm unit 112 are determined to have intruded into the intrusion prohibited region, the action instruction unit 145 issues an instruction to stop the movement of the arm unit 112 to the driving control unit 146, and issues an instruction to output a warning that the arm unit 112 has intruded into the intrusion prohibited region to the warning control unit 147. Accordingly, the intrusion of the arm unit 112 into the intrusion prohibited region is forcibly prevented, and the medical staff including the surgeon 201 and the like who have received the warning can continue the surgery while appropriately performing proper treatment.

In addition, in a case in which the microscope unit 111 and the arm unit 112 are determined to have intruded into the intrusion attention region, the action instruction unit 145 issues an instruction to operate the arm unit 112 to the driving control unit 146 so that the microscope unit 111 and the arm unit 112 can avoid the intrusion attention region (i.e., the microscope unit 111 and the arm unit 112 do not enter the intrusion attention region as possible as they can) with the position and the attitude of the microscope unit 111 maintained using a redundant degree of freedom, and issues an instruction to output a warning that the arm unit 112 has intruded into the intrusion attention region to the warning control unit 147. Accordingly, intrusion of the microscope unit 111 and the arm unit 112 into the intrusion attention region can be hindered as far as possible, and the medical staff including the surgeon 201 and the like who have received the warning can continue the surgery while paying attention to the movement of the microscope unit 111 and the arm unit 112.

In addition, in a case in which the microscope unit 111 and the arm unit 112 are determined to have intruded into the intrusion allowed region, the action instruction unit 145 issues an instruction to output a warning that the arm unit 112 has intruded into the intrusion allowed region to the warning control unit 147. Accordingly, the medical staff including the surgeon 201 and the like who have received the warning can continue the surgery while paying attention to the movement of the arm unit 112 and avoiding the microscope unit 111 and the arm unit 112.

Note that the action instruction unit 145 does not perform the process relating to the intrusion hindering action in a case in which the operation mode is the manual mode and the intrusion determination unit 144 does not perform the intrusion presence/absence determination process.

The driving control unit 146 controls driving of the arm unit 112 by driving the actuators provided at each of the joint units of the arm unit 112 in accordance with an operation of the surgeon 201. Similarly to the intrusion determination unit 144, the driving control unit 146 can ascertain a current attitude of the arm unit 112 on the basis of a detection value of the encoder provided at each joint unit of the arm unit 112 and the internal model of the arm unit 112 input to the control device 140 beforehand. In addition, the driving control unit 146 calculates a control value with respect to each joint unit that is likely to realize movement of the microscope unit 111 in accordance with an operation of the surgeon 201 on the basis of the ascertained current state of the arm unit 112 and details of the operation by the surgeon 201 recognized by the operation recognition unit 160, then drives each joint unit in accordance with the control value, and thereby causes the microscope unit 111 to have a desired position and attitude or the arm unit 112 to have a desired attitude.

Here, the driving control unit 146 performs different types of control in accordance with operation modes when performing driving control of the arm unit 112. First, in a case in which the operation mode of the arm unit 112 is the manual mode, the driving control unit 146 controls driving of the arm unit 112 such that the microscope unit 111 is moved through power assist control in accordance with a direct operation by the surgeon 201 through force control. For example, the driving control unit 146 drives the arm unit 112 through power assist control. In addition, even if the action instruction unit 145 issues an instruction at this time, the driving control unit 146 causes the arm unit 112 to operate in accordance with the direct operation by the surgeon 201, without performing control in accordance with the instruction.

On the other hand, in a case in which the operation mode of the arm unit 112 is the hands-free mode, the driving control unit 146 controls driving of the arm unit 112 such that the microscope unit 111 is moved through position control in accordance with an operation of the surgeon 201 input via the hands-free input device 150 and recognized by the operation recognition unit 160. In a case in which the action instruction unit 145 has issued an instruction at this time, however, the driving control unit 146 performs control in accordance with the instruction, regardless of the operation of the surgeon 201.

That is, in the case in which the arm unit 112 is determined to have intruded into the intrusion prohibited region, the driving control unit 146 stops the movement of the arm unit 112 in accordance with the instruction from the action instruction unit 145, regardless of the operation of the surgeon 201. In addition, in the case in which the arm unit 112 is determined to have intruded into the intrusion attention region, the driving control unit 146 changes the attitude of the arm unit 112 while maintaining the position and the attitude of the microscope unit 111 in accordance with the instruction from the action instruction unit 145 so that the arm unit 112 does not intrude into the intrusion attention region as far as possible, regardless of the operation of the surgeon 201.

The warning control unit 147 controls driving of the warning output unit 180 in accordance with an instruction from the action instruction unit 145, and causes a warning that the arm unit 112 has intruded into an intrusion appropriateness region to be output to the surgeon 201. Note that the warning control unit 147 can cause the output warning to stop in accordance with an arbitrary operation by the surgeon 201.

The functional configuration of the surgical system 10 according to the present embodiment has been described above. The intrusion appropriateness regions are set on the basis of the peripheral image of the microscope unit 111 and the arm unit 112 projecting the actual operation room, and the intrusion hindering action is executed at the time of driving control of the arm unit 112 in accordance with determination of the presence/absence of intrusion of the arm unit 112 into the set intrusion appropriateness regions according to the present embodiment as described above. Since a person or an object around the microscope unit 111 and the arm unit 112 can frequently move during surgery, by setting the intrusion appropriateness region in accordance with the actual situation, appropriate intrusion appropriateness regions in accordance with the actual situation can be set. Therefore, by executing the intrusion hindering action in accordance with determination of the presence/absence of intrusion of the arm unit 112 into the intrusion appropriateness regions set as described above, the intrusion hindering actions can be appropriately executed, and thus safer surgery can be realized.

Here, if the intrusion hindering action is executed so that interference of the arm unit 112 with every object around the arm unit is prevented, the range in which the arm unit 112 can move may be excessively restricted, and thus there is concern of smooth execution of the surgery being hindered. With regard to this matter, the plurality of types of intrusion appropriateness regions are set by stages in accordance with aspects of objects that can be interfered by the arm unit 112 in the present embodiment. In addition, different intrusion hindering actions are executed in accordance with the types of the intrusion appropriateness regions into which the arm unit 112 intrudes. Accordingly, the surgery can be smoothly executed while interference of the arm unit 112 with peripheral objects is appropriately hindered.

In addition, the intrusion presence/absence determination process is performed and the intrusion hindering action is executed only in the case in which the operation mode of the arm unit 112 is the hands-free mode in the present embodiment. The reason for this is that, for example, the surgeon 201 operates the arm unit 112 in direct contact with the microscope unit 111 or the arm unit 112 in the manual mode, and thus the surgeon 201 can operate the arm unit 112 while definitely ascertaining the movement of the arm unit 112. Thus, the surgeon 201 thinks that interference of the arm unit 112 with nearby objects can be avoided with his or her operation, without executing the intrusion hindering action, and therefore, the necessity for executing the intrusion hindering action in the manual mode becomes low. Rather, if the intrusion hindering action is executed in the manual mode, there is concern of an operation of the arm unit 112 by the surgeon 201 being excessively restricted, which impairs operability for the surgeon 201.

On the other hand, an aspect in which the surgeon 201 operates the arm unit 112, viewing display on the display device 120 in the hands-free mode, for example, so that the microscope unit 111 takes a position and an attitude at which an image of a desired operating site is likely to be obtained is considered. That is, in the hands-free mode, there is a high possibility of the surgeon 201 not paying attention to movement of the arm unit 112 itself. There is concern of the arm unit 112 being in unintentional contact with a nearby object in such a case, and thus the function of executing the intrusion hindering action to automatically prevent such contact is important.

As described above, by executing the intrusion hindering action only in the hands-free mode in which the surgeon 201 is highly likely not to ascertain movement of the arm unit 112 in the present embodiment, safer driving control of the arm unit 112 can be realized without impairing operability for the surgeon 201.

Note that the above-described functional configuration is merely an example, and the surgical system 10 may be able to execute the above-described process, and the functional may be arbitrary. Although, for example, various images relating to the settings of the intrusion appropriateness regions (the peripheral image, the peripheral image with distance information, and the image of the display screen relating to the GUI for the setting of the regions) are set to be displayed on the display device 120 on which the image of the operating site is displayed in the above-described configuration example, the present embodiment is not limited thereto. The surgical system 10 may be configured to include a separate display device from the display device 120 and the various images relating to the settings of the intrusion appropriateness regions may be displayed on the separate display device. Note that, in a case in which the various images relating to the settings of the intrusion appropriateness regions and the image of the operating site can be displayed on the same display device 120 together, switching of display of the images may be performed through an arbitrary operation by the surgeon 201.

In addition, although the process of setting the intrusion appropriateness regions are performed before the surgeon 201 performs treatment in the above-described configuration example, the present embodiment is not limited thereto. For example, in a case in which the surrounding situation significantly changes while treatment is performed, a process of re-setting the intrusion appropriateness regions may be performed while treatment is being performed. Accordingly, since the intrusion appropriateness regions can be set reflecting the latest situation, the intrusion appropriateness regions can be set more appropriately.

In addition, although the three types of regions including the intrusion prohibited region, the intrusion attention region, and the intrusion allowed region are set as the intrusion appropriateness regions in the above-described configuration example the present embodiment is not limited thereto. The way of dividing the stages when the intrusion appropriateness regions are set by stages may be arbitrary. For example, the number of types of regions other than three may be set as the intrusion appropriateness regions. Alternatively, the intrusion appropriateness regions may not be set by stages, and one type of region may be set as the intrusion appropriateness region.

Note that a specific device configuration of the control device 140 is not limited. The control device 140 may be configured to realize the above-described functions, and the specific device configuration may be arbitrary. For example, the control device 140 may be constituted by one device or may be constituted by a plurality of devices. In the case in which the control device 140 constituted by a plurality of devices, for example, if the functions schematically shown by the blocks in FIG. 2 are distributed and mounted in the plurality of devices and the plurality of devices are connected to communicate with each other to operate in cooperation with each other, functions similar to those of the control device 140 can be realized.

In addition, a computer program for realizing each of the functions of the control device 140 of the surgical system 10 illustrated in FIG. 2 can be produced can installed in a processing device such as a PC. In addition, a computer-readable recording medium storing such a computer program can also be provided. The recording medium is, for example, a magnetic disk, an optical disc, a magneto-optical disc, a flash memory, or the like. In addition, the computer program may be distributed via, for example, a network, without using a recording medium.

2. CONTROL METHOD

Figure 6A:
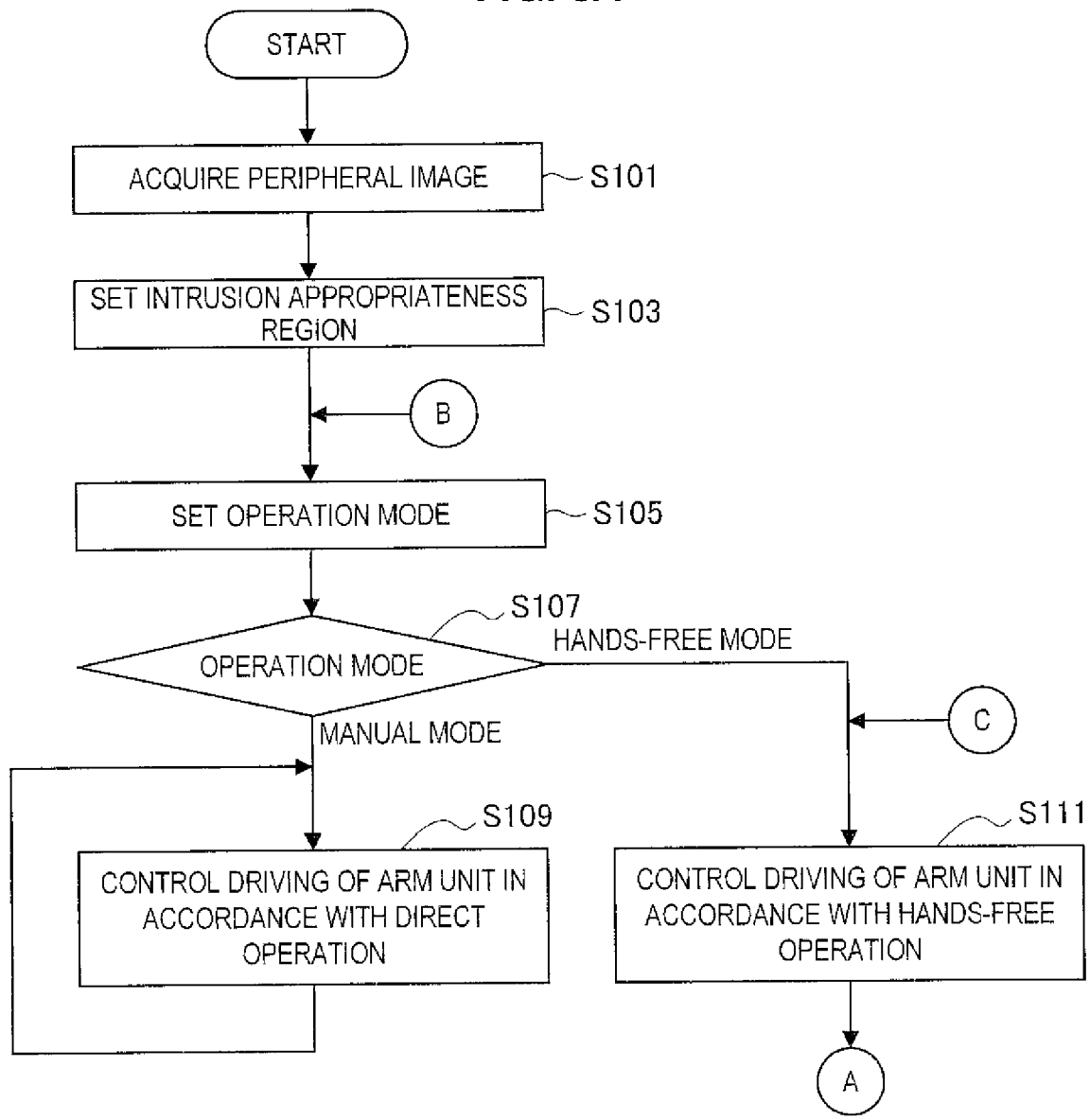
FIG. 6A is a flowchart illustrating an example of a processing procedure of a control method according to the present embodiment.
Figure 6B:
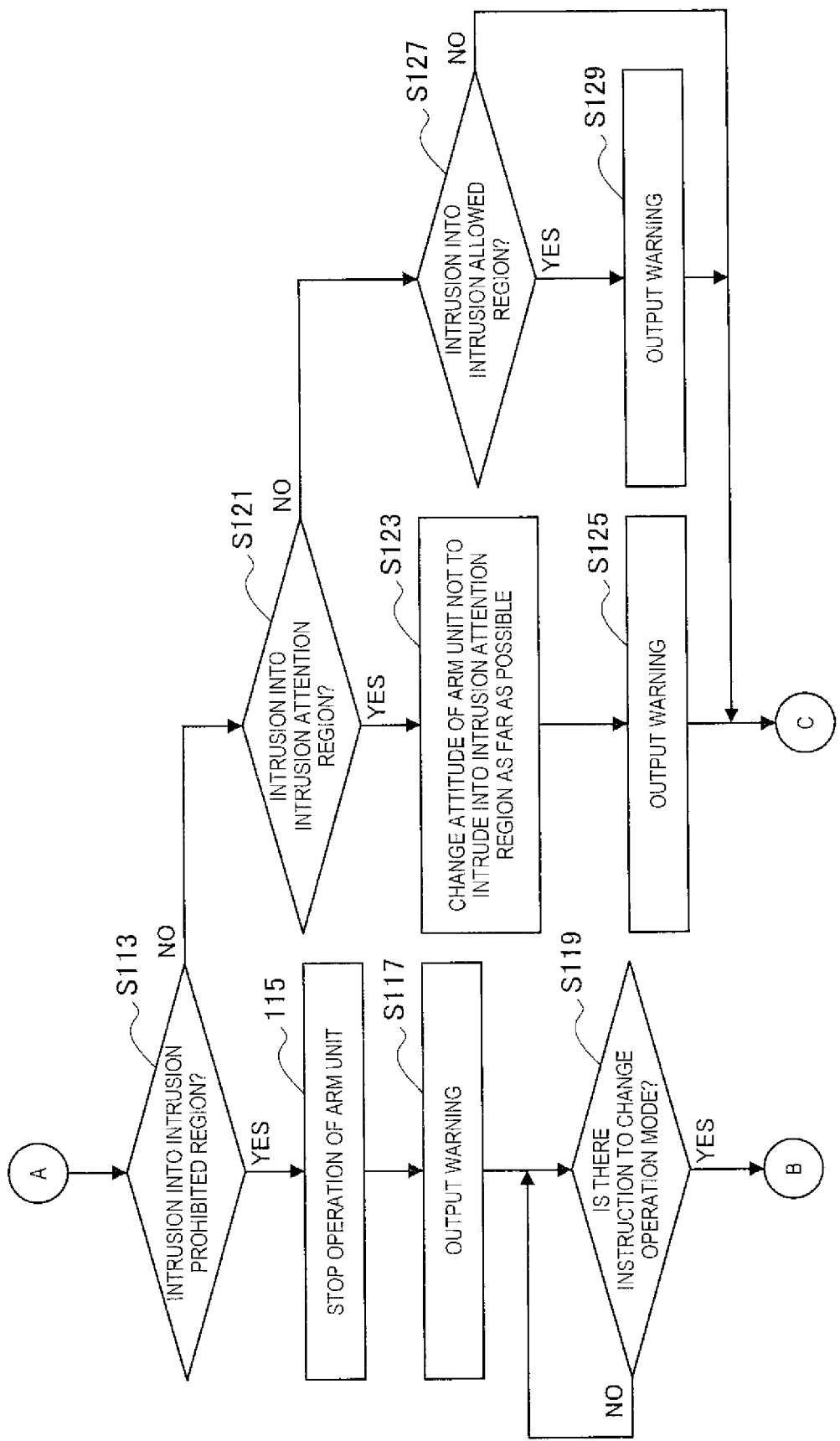
FIG. 6B is a flowchart illustrating the example of the processing procedure of the control method according to the present embodiment.

A processing procedure of a control method according to the present embodiment will be described with reference to FIGS. 6A and 6B. FIGS. 6A and 6B are flowcharts illustrating an example of the processing procedure of the control method according to the present embodiment. Note that each of the processes shown in FIGS. 6A and 6B corresponds to the processes executed by the control device 140 of the surgical system 10 illustrated in FIG. 2. Since details of the processes have already been described in the description of the functional configuration of the surgical system 10, detailed description of each process will be omitted in the following description of the processing procedure of the control method.

In addition, it is assumed that surgical settings are completed before the series of processes illustrated in FIGS. 6A and 6B are executed. That is, the control method according to the present embodiment is started in the stage in which preparation for surgery is completed to the extent that the surgeon 201 can start treatment on an operating site at any time.

Referring to FIGS. 6A and 6B, first a peripheral image is acquired in the control method according to the present embodiment (Step S101). The process indicated in Step S101 corresponds to the process of transmitting information of the peripheral image from the peripheral image acquisition camera 130 illustrated in FIG. 2 to the image processing unit 141 of the control device 140.

Next, intrusion appropriateness regions are set (Step S103). Specifically, in Step S103, for example, an intrusion prohibited region, an intrusion attention region, and an intrusion allowed region are set as intrusion appropriateness region in accordance with an instruction from the surgeon 201 given by using the GUI illustrated in FIG. 5. Note that the process indicated in Step S103 corresponds to the process executed by the region setting unit 142 illustrated in FIG. 2.

The processes of Step S101 and Step S103 described above are processes executed before the surgeon 201 starts treatment on the operating site. On the other hand, the processes from Step S105 which will be described below are processes executed after the surgeon 201 starts treatment on the operating site.

In Step S105, the operation mode of the arm unit 112 of the observation device 110 is set in accordance with an operation of the surgeon 201. The process indicated in Step S105 corresponds to the process executed by the operation mode setting unit 143 illustrated in FIG. 2. Note that, in the present embodiment, an instruction to change the operation mode may be input by the surgeon 201 at an arbitrary timing in the series of processes performed after Step S105. In the case in which the instruction is input, the process returns to Step S105, and the process of setting the operation mode in accordance with the instruction is performed.

Next, the operation mode is determined (Step S107). In the case in which the operation mode is the manual mode, the process proceeds to Step S109, and driving of the arm unit 112 is controlled in accordance with a direct operation by the surgeon 201. In this case, the process of Step S109 is repeatedly executed (i.e., the driving control of the arm unit 112 continues in the manual mode) until an instruction to end control or an instruction to change the operation mode from the surgeon 201 is input.

On the other hand, in the case in which the operation mode is the hands-free mode, the process proceeds to Step S111, and driving of the arm unit 112 is controlled in accordance with a hands-free operation by the surgeon 201. Note that the processes indicated in Steps S107 to S111 above correspond to the process executed by the driving control unit 146 illustrated in FIG. 2.

In Step S111, it is determined whether the microscope unit 111 and the arm unit 112 have intruded into the intrusion prohibited region while driving of the arm unit 112 is controlled in accordance with the hands-free operation (Step S113). The process indicated in Step S113 corresponds to the process executed by the intrusion determination unit 144 illustrated in FIG. 2.

In a case in which it is determined that the arm unit 112 has intruded into the intrusion prohibited region in Step S113, the operation of the arm unit 112 is stopped (Step S115), and a warning that the microscope unit 111 and the arm unit 112 have intruded into the intrusion prohibited region is output (Step S117). The processes indicated in Steps S115 and S117 correspond to the processes executed by the driving control unit 146 and the warning control unit 147 in accordance with an instruction issued by the action instruction unit 145 illustrated in FIG. 2.

When the warning is output in Step S117, it is next determined that whether an instruction to change the operation mode from the surgeon 201 is to be input (Step S119). When the instruction is not input, the system stands by until the instruction is given while the operation of the arm unit 112 is stopped and the warning is continuously output. On the other hand, in a case in which the instruction is input, the process returns to Step S105, and the operation mode is set again in accordance with the instruction. In this case, since the operation mode shifts from the hands-free mode to the manual mode, the processes of Steps S107 and S109 are executed, and thus the surgeon 201 can move the arm unit 112 through a direct operation. At this time, the waning can also be stopped along with the switch of the operation mode. That is, in the case in which the arm unit 112 is determined to have intruded into the intrusion prohibited region and thus the operation of the arm unit 112 is stopped, the surgeon 201 can move the arm unit 112 and continue the surgery by switching the operation mode in the present embodiment.

On the other hand, in a case in which it is determined that the microscope unit 111 and the arm unit 112 have not intruded into the intrusion prohibited region in Step S113, the process proceeds to Step S121, and it is determined whether the microscope unit 111 and the arm unit 112 have intruded into the intrusion attention region. The process indicated in Step S121 corresponds to the process executed by the intrusion determination unit 144 illustrated in FIG. 2.

In a case in which it is determined that the microscope unit 111 and the arm unit 112 have intruded into the intrusion attention region in Step S121, the attitude of the arm unit 112 is changed not to intrude the intrusion attention region as far as possible while the position and the attitude of the microscope unit 111 are maintained (Step S123), and a warning that the microscope unit 111 and the arm unit 112 have intruded into the intrusion attention region is output (Step S125). The processes indicated in Steps S123 and S125 correspond to the processes executed by the driving control unit 146 and the warning control unit 147 in accordance with an instruction issued by the action instruction unit 145 illustrated in FIG. 2.

In the case in which the microscope unit 111 and the arm unit 112 have intruded into the intrusion attention region, the surgeon 201 can continue the operation of the arm unit 112 through a hands-free operation. Thus, after the warning is output in Step S125, the process returns to Step S111, and driving control of the arm unit 112 is continuously executed in accordance with the hands-free operation. Note that, in a case in which it can be determined that there is no safety problem while the microscope unit 111 and the arm unit 112 have intruded into the intrusion attention region, the warning may be appropriately stopped through an arbitrary operation by the surgeon 201.

In a case in which it is determined that the microscope unit 111 and the arm unit 112 have not intruded into the intrusion attention region in Step S121, the process proceeds to Step S127, and it is determined whether the microscope unit 111 and the arm unit 112 have intruded into the intrusion allowed region. The process indicated in Step S127 corresponds to the process executed by the intrusion determination unit 144 illustrated in FIG. 2.

In a case in which it is determined that the microscope unit 111 and the arm unit 112 have intruded into the intrusion allowed region in Step S127, a warning that the microscope unit 111 and the arm unit 112 have intruded into the intrusion allowed region is output (Step S129). The process indicated in Step S129 corresponds to the process executed by the warning control unit 147 in accordance with an instruction issued by the action instruction unit 145 illustrated in FIG. 2.

In the cases in which the microscope unit 111 and the arm unit 112 have intruded and have not intruded into the intrusion allowed region, the surgeon 201 can continue the operation of the arm unit 112 through a hands-free operation. Thus, after the warning is output in Step S129 or in the case in which it is determined that the microscope unit 111 and the arm unit 112 have not intruded into the intrusion allowed region in Step S127, the process returns to Step S111, and driving control of the arm unit 112 in accordance with the hands-free operation is continuously executed. Note that, it can be determined that there is no safety problem while the arm unit 112 has intruded into the intrusion allowed region, the warning may be appropriately stopped through an arbitrary operation by the surgeon 201.

The processing procedure of the control method according to the present embodiment has been described above with reference to FIGS. 6A and 6B.

3. MODIFIED EXAMPLE

Figure 7:
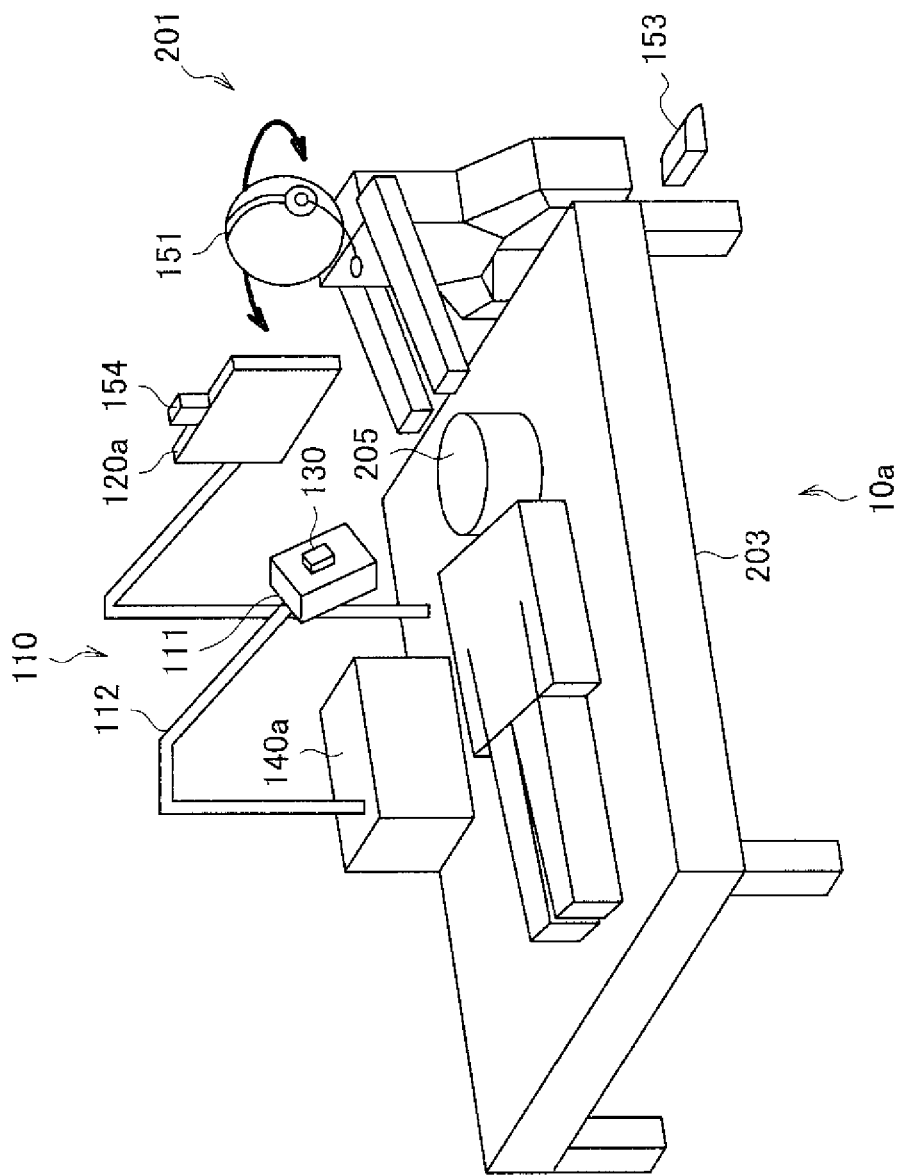
FIG. 7 is a diagram illustrating a schematic configuration of a surgical system according to a modified example of the present embodiment.

A modified example of the above-described embodiment will be described. FIG. 7 is a diagram illustrating a schematic configuration of a surgical system according to a modified example of the present embodiment.

Referring to FIG. 7, the surgical system 10a according to the modified example of the present embodiment includes an observation device 110, a display device 120a, a peripheral image acquisition camera 130, a control device 140a, a microphone 151, a foot switch 153, and an operation recognition camera 154. The surgical system 10a according to the present modified example corresponds to a system configured by changing the configurations of the display device 120 and the control device 140 of the above-described surgical system 10 and not having the eyeglass-type wearable device 152 as described above. In addition, the marker 155 is not provided on the surgeon 201 either. Other matters with respect to the surgical system 10a are similar to the above-described surgical system 10. Therefore, in the following description of the surgical system 10a, matters different from the surgical system 10 will be mainly described, and detailed description of overlapping matters will be omitted.

In the present modified example, the display device 120a is disposed in a relatively short distance from the surgeon 201 as illustrated. For example, the display device 120a is disposed in front of the eyes of the surgeon 201 above the patient bed 203. The display device 120a is a naked-eye 3D display, and the surgeon 201 can observe an operating site on the display device 120a in stereoscopic view without wearing a separate device such as the eyeglass-type wearable device 152.

In addition, the operation recognition camera 154 is also disposed in a relatively short distance from the surgeon 201 in accordance with the disposition position of the display device 120a in the present modified example. Thus, the control device 140a can detect a line of sight of the surgeon 201 on the basis of an image captured by the operation recognition camera 154. In addition, since the distance between the operation recognition camera 154 and the surgeon 201 is short, the control device 140a can accurately recognize a head track of the surgeon 201 on the basis of the image captured by the operation recognition camera 154, even without the marker 155.

Since matters with respect to the configuration and the function of the control device 140a other than the above-described methods of recognizing a line of sight and a head track of the surgeon 201 are similar to those of the control device 140 illustrated in FIG. 2, description thereof will be omitted.

The schematic configuration of the surgical system 10a according to the modified example of the present embodiment has been described above.

4. CONFIGURATION EXAMPLE OF OBSERVATION DEVICE

Figure 8:
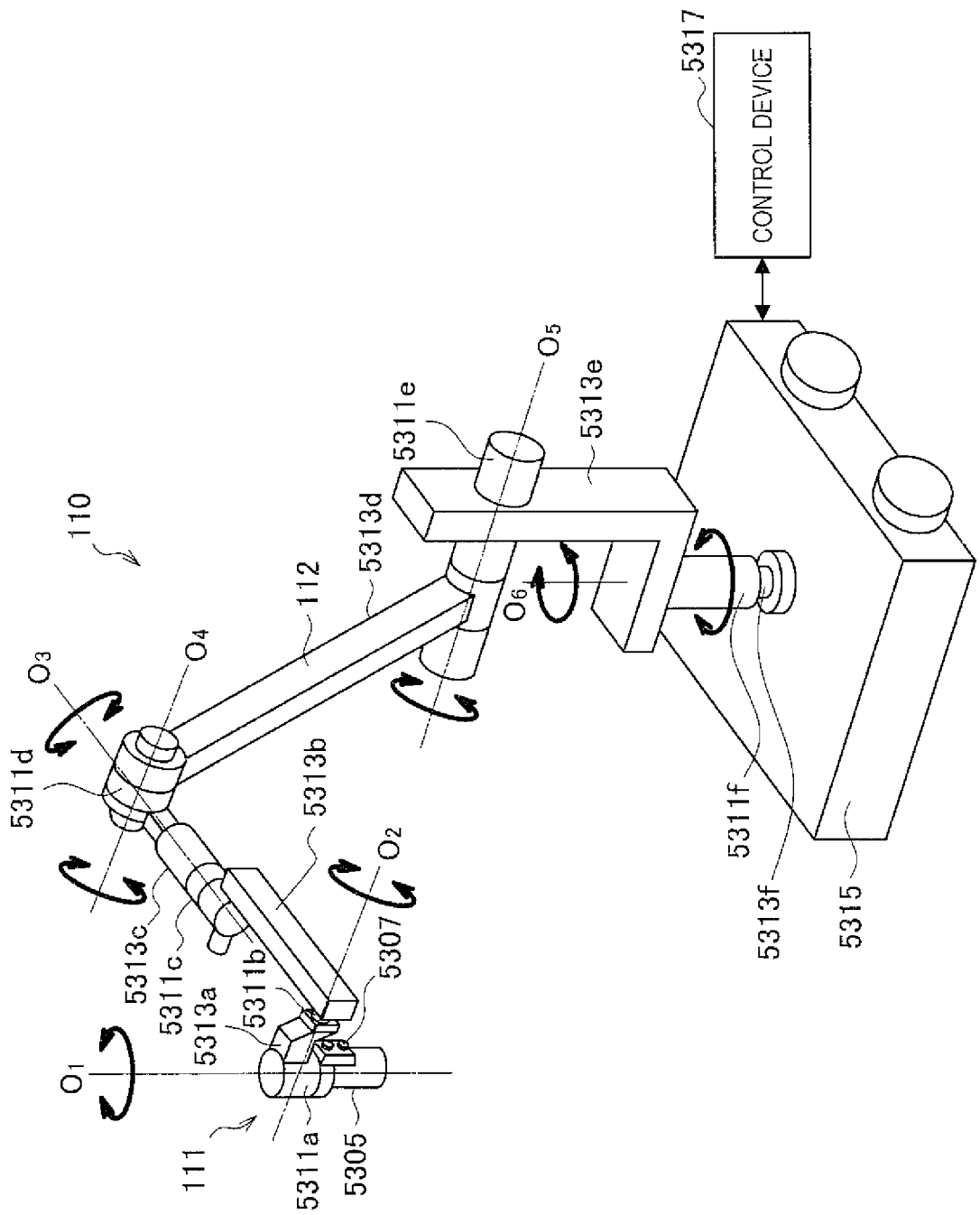
FIG. 8 is an exterior diagram illustrating a configuration example of an observation device according to the present embodiment.

A specific configuration example of the above-described observation device 110 will be described. FIG. 8 is an exterior diagram illustrating a configuration example of the observation device 110 according to the present embodiment. Note that, although the observation device 110 has the arm unit 112 of which a base end is connected to the patient bed 203 in the schematic diagrams illustrated in FIGS. 1 and 7, a configuration example in which a base part 5315 grounded with a floor surface, which will be described below, is provided and the base end of the arm unit 112 is connected to the base part 5315 as illustrated in FIG. 8. In addition, in FIG. 8, the configuration of the observation device 110 with the arm unit 112 having six degrees of freedom with respect to movement of the microscope unit 111 is illustrated as an example. However, the arm unit 112 of the observation device 110 may be configured to have redundant degrees of freedom as described above.

Referring to FIG. 8, the observation device 110 has the microscope unit 111 for enlarging and observe an observation target (an operating site of the patient 205), the arm unit 112 supporting the microscope unit 111 at its tip, a base part 5315 supporting the base end of the arm unit 112, and a control device 5317 that comprehensively control operations of the observation device 110.

The microscope unit 111 is made up of an approximately cylindrical barrel unit 5305, an imaging unit (not illustrated) provided inside the barrel unit 5305, and an operating unit 5307 provided in a partial region on the outer circumference of the barrel unit 5305.

The aperture on the bottom end of the barrel unit 5305 is provided with a cover glass that protects the imaging unit inside. Observation light passes through the cover glass and is incident on the imaging unit inside the barrel unit 5305. Note that a light source made up of a light-emitting diode (LED) or the like, for example, may also be provided inside the barrel unit 5305, and during imaging, light may be radiated from the light source onto the observation target through the cover glass.

The imaging unit is made up of an optical system that condenses observation light, and an image sensor that senses the observation light condensed by the optical system. The optical system is made up of a combination of multiple lenses, including a focus lens and a zoom lens, the optical characteristics of which are adjusted so that an image of the observation light is formed on the light-sensitive face of the image sensor. The image sensor senses and photoelectrically converts the observation light to thereby generate an image signal corresponding to the observed image. A sensor capable of color photography including a Bayer array, for example, is used as the image sensor. The image sensor may be any of various known types of image sensors, such as a complementary metal-oxide-semiconductor (CMOS) image sensor or a charge-coupled device (CCD) image sensor. The image signal generated by the image sensor is transmitted to the control device 5317 as RAW data. At this point, the transmission of the image signal may be conducted favorably by optical communication. This is because at the surgery venue, the surgeon performs surgery while observing the state of the affected area via the captured image, and thus for safer and more reliable surgery, there is demand for the moving image of the operating site to be displayed as close to real-time as possible. Transmitting the image signal by optical communication makes it possible to display the captured image with low latency.

Note that the imaging unit may also include a driving mechanism that moves the focus lens and the zoom lens of the optical system along the optical axis. By suitably moving the zoom lens and the focus lens with the driving mechanism, the focus distance during imaging and the magnification factor of the captured image may be adjusted. Also, the imaging unit may be provided with any of various types of functions typically provided in electronic imaging microscope units, such as an auto exposure (AE) function, an auto focus (AF) function or the like.

In addition, the imaging unit is configured to have a pair of image sensors for acquiring image signals for right eye and left eye each corresponding to stereoscopic view (3D display). Due to 3D display, the operator can ascertain the depth of a biological tissue of the operating site more accurately. Note that, in a case in which the imaging unit is configured to be a multi-plate type, a plurality of optical systems can be provided corresponding to each of the image sensors. However, the present embodiment is not limited thereto, and the imaging unit may be configured as a so-called single-plate imaging unit having one image sensor, or may be configured as a so-called multi-plate imaging unit having one or more image sensors. In the case in which the imaging unit is configured to be a multi-plate type, for example, image signals each corresponding to R, G, and B are generated by each of the image sensors, the signals may be combined, and thereby a color image is obtained.

The operating unit 5307 is constituted by, for example, a 4-direction lever, a switch, or the like, and is an input means that receives operation input of the surgeon 201. For example, the surgeon 201 can input an instruction to change a focal distance to an observation target of an observation image and an enlargement magnification via the operating unit 5307. When the driving mechanism of the imaging unit appropriately moves the zoom lens and the focus lens in accordance with the instruction, the focal distance and the enlargement magnification can be adjusted. In addition, in the case in which the operation mode of the arm unit 112 is the manual mode, for example, the surgeon 201 can input an instruction to further shift the operation mode to one of an all-free mode and a locked mode, which will be described below, via the operating unit 5307. Note that, in a case in which the surgeon 201 attempts to move the microscope unit 111 in the manual mode, an aspect in which the surgeon 201 moves the microscope unit 111, holding the barrel unit 5305 is assumed. Thus, it is preferable for the operating unit 5307 to be provided at a position at which the surgeon 201 can easily operate the operating unit with his or her finger, holding the barrel unit 5305 so that the surgeon 201 can operate it while moving the barrel unit 5305.

The arm unit 112 is configured as a result of multiple links (a first link 5313*a* to a sixth link 5313*f*) being rotatably joined to each other by multiple joint units (a first joint unit 5311*a* to a sixth joint unit 5311*f*).

The first joint unit 5311*a* has an approximately cylindrical shape, and on the leading end (bottom end) thereof supports the top end of the barrel unit 5305 of the microscope unit 111, so as to allow rotation about a rotation axis (first axis $O_1$) parallel to the central axis of the barrel unit 5305. Herein, the first joint unit 5311*a* may be configured so that the first axis $O_1$ is aligned with the optical axis of the imaging unit of the microscope unit 111. Consequently, rotating the microscope unit 111 about the first axis $O_1$ makes it possible to change the field of view as though rotating the captured image.

The first link 5313*a* securely supports the first joint unit 5311*a* on the leading end thereof. Specifically, the first link 5313*a* is an approximately L-shaped rod-like member, the leading edge of which extends in a direction orthogonal to the first axis $O_1$, while also being connected to the first joint unit 5311*a* so that the end of that edge abuts the top end on the outer circumference of the first joint unit 5311*a*. The second joint unit 5311*b* is connected to the end of the base edge of the approximate L-shape of the first link 5313*a*.

The second joint unit 5311*b* has an approximately cylindrical shape, and on the leading end thereof supports the base end of the first link 5313*a*, so as to allow rotation about a rotation axis (second axis $O_2$) orthogonal to the first axis $O_1$. The leading end of the second link 5313*b* is securely connected to the base end of the second joint unit 5311*b*.

The second link 5313*b* is an approximately L-shaped rod-like member, the leading edge of which extends in a direction orthogonal to the second axis $O_2$, while the end of that edge is securely connected to the base end of the second joint unit 5311*b*. The third joint unit 5311*c* is connected to the base edge of the approximate L-shape of the second link 5313*b*.

The third joint unit 5311*c* has an approximately cylindrical shape, and on the leading end thereof supports the base end of the second link 5313*b*, so as to allow rotation about a rotation axis (third axis $O_3$) orthogonal to both the first axis $O_1$ and the second axis $O_2$. The leading end of the third link 5313*c* is securely connected to the base end of the third joint unit 5311*c*. By rotating the configuration on the leading-end side, including the microscope unit 111, about the second axis $O_2$ and the third axis $O_3$, the microscope unit 111 may be moved to change the position of the microscope unit 111 on the horizontal plane. In other words, controlling the rotation about the second axis $O_2$ and the third axis $O_3$ makes it possible to move the field of view of the captured image on a flat plane.

The third link 5313*c* is configured to have an approximately cylindrical shape on the leading end side, and on the leading end of the cylindrical shape, the base end of the third joint unit 5311*c* is securely connected so that both have approximately the same central axis. The base end side of the third link 5313*c* has a rectangular column shape, and the fourth joint unit 5311*d* is connected to the end thereof.

The fourth joint unit 5311*d* has an approximately cylindrical shape, and on the leading end thereof supports the base end of the third link 5313*c*, so as to allow rotation about a rotation axis (fourth axis $O_4$) orthogonal to the third axis $O_3$. The leading end of the fourth link 5313*d* is securely connected to the base end of the fourth joint unit 5311*d*.

The fourth link 5313*d* is a rod-like member that extends approximately linearly in a direction orthogonal to the fourth axis $O_4$, while also being securely connected to the fourth joint unit 5311*d* so that the leading end abuts the side face of the approximately cylindrical shape of the fourth joint unit 5311*d*. The fifth joint unit 5311*e* is connected to the base end of the fourth link 5313*d*.

The fifth joint unit 5311*e* has an approximately cylindrical shape, and on the leading end side thereof supports the base end of the fourth link 5313*d*, so as to allow rotation about a rotation axis (fifth axis $O_5$) parallel to the fourth axis $O_4$. The leading end of the fifth link 5313*e* is securely connected to the base end of the fifth joint unit 5311*e*. The fourth axis $O_4$ and the fifth axis $O_5$ are rotation axes enabling the microscope unit 111 to be moved in the vertical direction. By rotating the configuration on the leading-end side, including the microscope unit 111, about the fourth axis $O_4$ and the fifth axis $O_5$, the height of the microscope unit 111, or in other words the distance between the microscope unit 111 and the observation target, may be adjusted.

The fifth link 5313*e* is made up of a combination of a first member having an approximate L-shape with one edge extending in the vertical direction while the other edge extends in the horizontal direction, and a rod-like second member that extends vertically downward from the unit of the first member that extends in the horizontal direction. The base end of the fifth joint unit 5311*e* is securely connected near the top end of the unit of the first member that extends in the vertical direction of the fifth link 5313*e*. The sixth joint unit 5311*f* is connected to the base end (bottom end) of the second member of the fifth link 5313*e*.

The sixth joint unit 5311*f* has an approximately cylindrical shape, and on the leading end side thereof supports the base end of the fifth link 5313*e*, so as to allow rotation about a rotation axis (sixth axis $O_6$) parallel to the vertical direction. The leading end of the sixth link 5313*f* is securely connected to the base end of the sixth joint unit 5311*f*.

The sixth link 5313*f* is a rod-like member that extends in the vertical direction, with the base end securely connected to the top face of the base unit 5315.

The allowable rotation range of the first joint unit 5311*a* to the sixth joint unit 5311*f* is suitably set so that the microscope unit 111 is capable of desired motion. Consequently, in the arm unit 112 having the configuration described above, three degrees of translational freedom and three degrees of rotational freedom, for a total of six degrees of freedom, may be realized for the motion of the microscope unit 111. In this way, by configuring the arm unit 112 so that six degrees of freedom are realized for the motion of the microscope unit 111, it becomes possible to freely control the position and the attitude of the microscope unit 111 within the movable range of the arm unit 112. Consequently, it becomes possible to observe an operating site from any angle, and surgery may be executed more smoothly.

Note that the configuration of the arm unit 112 illustrated in the diagram is merely one example, and factors such as the number and the shapes (lengths) of the links constituting the arm unit 112, as well as the number and arrangement of the joint units and the directions of the rotation axes may be designed suitably so that the desired degrees of freedom may be realized. For example, as described above, to move the microscope unit 111 freely, the arm unit 112 preferably is configured to have six degrees of freedom, but the arm unit 112 may also be configured to have more degrees of freedom (in other words, redundant degrees of freedom). When redundant degrees of freedom exist, in the arm unit 112, it becomes possible to change the attitude of the arm unit 112 while keeping the position and the attitude of the microscope unit 111 in a locked state. Thus, more convenient control for the operator can be realized, like controlling an attitude of the arm unit 112 so that the microscope unit 111 and the arm unit 112 do not intrude into the intrusion attention region as far as possible, or the like, unlike the above-described case in which the microscope unit 111 and the arm unit 112 intrude into the intrusion attention region.

Herein, the first joint unit 5311a to the sixth joint unit 5311f may be provided with actuators equipped with a driving mechanism such as a motor, an encoder that detects the rotation angle in each joint unit, and the like. In addition, by having the control device 5317 suitable control the driving of each actuator provided for the first joint unit 5311a to the sixth joint unit 5311f, the attitude of the arm unit 112, or in other words the position and the attitude of the microscope unit 111, may be controlled. Specifically, the control device 5317 is able to ascertain the current state of the arm unit 112 on the basis of information about the rotation angle of each joint unit detected by the encoder. The control device 5317 calculates a control value of each joint unit that is likely to realize movement of the microscope unit 111 in accordance with the operation by the surgeon 201 on the basis of the ascertained current state of the arm unit 112 and drives the driving mechanism of each joint unit in accordance with the control value.

In the case in which the operation mode of the arm unit 112 is the manual mode, for example, the control device 5317 appropriately controls driving of the arm unit 112 in accordance with a direct operation by the surgeon 201 through force control, and thus the position and the attitude of the microscope unit 111 are controlled as described above. In addition, in the case in which the operation mode of the arm unit 112 is the hands-free mode, for example, the control device 5317 appropriately controls driving of the arm unit 112 in accordance with a hands-free operation by the surgeon 201 through position control, and thus the position and the attitude of the microscope unit 111 are controlled.

In addition, driving of the arm unit 112 may be controlled such that the arm unit performs a pivot motion. Here, the pivot motion is to move the microscope unit 111 such that the optical axis of the microscope unit 111 faces a predetermined point (which will also be referred to as a pivot point) in a space at all times. Since the same observation position can be observed in various directions in the pivot motion, an affected area can be observed more closely.

In addition, the first joint unit 5311a to the sixth joint unit 5311f may also be provided with brakes that restrain rotation. The operation of such brakes may be controlled by the control device 5317. For example, when it is desirable to lock the position and the attitude of the microscope unit 111, the control device 5317 applies the brake on each joint unit. As a result, the attitude of the arm unit 112, or in other words the position and the attitude of the microscope unit 111, may be locked without driving the actuators, and power consumption may be reduced. When it is desirable to move the position and the attitude of the microscope unit 111, it is sufficient for the control device 5317 to release the brake on each joint unit and suitably drive the actuators in accordance with an operation of the surgeon 201.

Such a brake operation may be performed in response to operation performed by the surgeon 201 via the operating unit 5307 described above. When the user wants to move the position and the attitude of the microscope unit 111, the surgeon 201 operates the operating unit 5307 to release the brake on each joint unit. As a result, the operation mode of the arm unit 112 switches to a mode allowing each joint unit to be rotated freely (all-free mode). Meanwhile, when the surgeon 201 wants to lock the position and the attitude of the microscope unit 111, the user operates the operating unit 5307 to apply the brake on each joint unit. As a result, the operation mode of the arm unit 112 switches to a mode in which the rotation of each joint unit is restrained (locked mode).

The control device 5317 controls operations of the observation device 110. For example, the control device 5317 controls driving of the arm unit 112 by causing actuators of the first joint unit part 5311a to the sixth joint unit part 5311f to operate in accordance with an operation of the surgeon 201. In addition, by, controlling operations of the brakes of the first joint unit part 5311a to the sixth joint unit part 5311f, for example, the control device 5317 changes the operation mode of the arm unit 112 between the all-free mode and the locked mode. In addition, the control device 5317 adjusts, for example, photographing conditions (a focal distance and an enlargement magnification) of the imaging unit of the microscope unit 111 of the observation device 110. In addition, the control device 5317 performs, for example, various kinds of signal processing on an image signal acquired by the imaging unit of the microscope unit 111 of the observation device 110, and causes the display device 120 (not illustrated in FIG. 8) to display an image of the operating site on the basis of the image data.

Note that the communication between the control device 5317 and the microscope unit 111, as well as the communication between the control device 5317 and the first joint unit 5311a to the sixth joint unit 5311f, may be wired communication or wireless communication. In the case of wired communication, communication using electrical signals may be conducted, or optical communication may be conducted. In this case, the transmission cable used for wired communication may be configured as an electrical signal cable, optical fiber, or a composite cable of the two, in accordance with the communication method. Meanwhile, in the case of wireless communication, it is no longer necessary to lay down a transmission cable inside the operating room, and thus a situation in which the movement of medical staff inside the operating room is impeded by such a transmission cable may be resolved.

The control device 5317 may be a processor such as a central processing unit (CPU) or a graphics processing unit (GPU), a control board on which a processor and a storage element such as a memory are both mounted, or the like. As a result of the processor of the control device 5317 operating in accordance with a certain program, the various functions described above may be realized. Note that, in the example illustrated in the diagram, the control device 5317 is provided as a separate device from the observation device 110, but the control device 5317 may also be unified with the observation device 110, such as by being installed inside the base unit 5315 of the observation device 110, for example. Alternatively, the control device 5317 may be made up of multiple devices. For example, by providing a control board or the like in the microscope unit 5303 and each of the first joint unit 5311a to the sixth joint unit 5311f of the arm unit 5309, and communicably connecting these control boards to each other, functions similar to the control device 5317 may be realized.

Here, the control device 5317 can be the same as the control devices 140 of the above-described surgical systems 10 and 10*a*. That is, the control device 5317 may have similar functions to those of the control devices 140, control operations of the observation device 110, and comprehensively control operations of the surgical systems 10 and 10*a*.

The specific configuration example of the observation device 110 according to the present embodiment have been described above.

5. SUPPLEMENT

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Although the intrusion hindering action is performed when the operator operates the arm unit through the hands-free operation in the above-described embodiment, for example, the technology according to the present disclosure is not limited thereto. For example, the technology according to the present disclosure may be applied to a surgical system in which an arm unit is operated in a master-slave scheme. Since an operator remotely operates the arm unit in the master-slave scheme, the operator can operate the arm unit without directly viewing the arm unit, similarly to the hands-free operation. Thus, since the technology according to the present disclosure is applied, similar effects can be obtained. As described, the technology according to the present disclosure can be preferably applied to the surgical system in which an operator operates an arm unit without being in contact with the arm unit.

In addition, although an operation of the arm unit to avoid intrusion into the intrusion appropriateness region and output of a warning are performed as the intrusion hindering action in the above-described embodiment, for example, the technology according to the present disclosure is not limited thereto. In the technology according to the present disclosure, the intrusion hindering action may be an action that can hinder intrusion of the arm unit into the intrusion appropriateness region, and a type thereof is not limited. As the intrusion hindering action, for example, only one of the operation of the arm unit to avoid intrusion into the intrusion appropriateness region and output of a warning may be performed. Alternatively, other than the warning, various actions giving an alert for intrusion of the arm unit into the intrusion appropriateness region to the operator may be performed as the intrusion hindering action. As an action giving an alert for intrusion of the arm unit into the intrusion appropriateness region to the operator, for example, an action of gradually decreasing an operation speed of the arm unit as the arm unit gets closer to the intrusion appropriateness region or the like is considered. Since the operation speed of the microscope unit 111 decreases if the operation speed of the arm unit decreases, a speed of movement of the visual field with respect to the image of the operating site viewed by the operator becomes lower accordingly. The operator can recognize that the arm unit is getting closer to the intrusion appropriateness region since the speed of movement of the visual field with respect to the image of the operating site becomes lower. In addition, as the intrusion hindering action, every action used as feedback to an operator when any alert is generally given to the operator in an operation of a support arm device may be employed.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control device including:

a driving control unit configured to control driving of an arm unit that supports a medical instrument;

a region setting unit configured to set an intrusion appropriateness region for which appropriateness of intrusion of the medical instrument or the arm unit is determined in a space on a basis of a peripheral image showing a peripheral state of the medical instrument or the arm unit;

an intrusion determination unit configured to determine presence/absence of intrusion of the medical instrument or the arm unit into the intrusion appropriateness region when the driving control unit controls driving of the arm unit in accordance with a non-contact operation by a user with respect to the arm unit; and an action instruction unit configured to cause an intrusion hindering action for hindering intrusion of the medical instrument or the arm unit into the intrusion appropriateness region to be executed in accordance with a determination result of the intrusion determination unit.

(2)

The control device according to (1), in which the intrusion hindering action is at least any of an operation of the arm unit to avoid intrusion into the intrusion appropriateness region or output of a warning.

(3)

The control device according to (1) or (2), in which the intrusion appropriateness region includes at least any of an intrusion prohibited region that is a region into which the medical instrument or the arm unit is prohibited from intruding within a movable range of the arm unit, an intrusion attention region that is a region into which the medical instrument or the arm unit is allowed to partially intrude within the movable range of the arm unit, or an intrusion allowed region that is a region into which the medical instrument or the arm unit is allowed to intrude within the movable range of the arm unit.

(4)

The control device according to (3), in which the peripheral image includes a state inside an operating room, and the intrusion prohibited region includes a region in which at least any of a patient or a surgical apparatus near a patient bed is present.

(5)

The control device according to (3), in which the peripheral image includes a state inside an operating room, and the intrusion attention region includes a region in which at least any of a cable suspended in the operating room or a cloth suspended in the operating room is present.

(6)

The control device according to (3), in which the peripheral image includes a state inside an operating room, and the intrusion allowed region includes a region in which medical staff is present.

(7)

The control device according to any one of (3) to (6), in which, in a case in which the intrusion determination unit determines that the medical instrument or the arm unit has intruded into the intrusion prohibited region, the action instruction unit issues an instruction to stop an operation of the arm unit and an instruction to output a warning.

(8)

The control device according to any one of (3) to (7), in which the arm unit is configured to have a redundant degree of freedom with respect to movement of the medical instrument, and in a case in which the intrusion determination unit determines that the medical instrument or the arm unit has intruded into the intrusion attention region, the action instruction unit issues an instruction to cause the arm unit to operate such that the arm unit does not intrude into the intrusion attention region while a position and an attitude of the medical instrument are maintained and an instruction to output a warning.

(9)

The control device according to any one of (3) to (8), in which, in a case in which the intrusion determination unit determines that the medical instrument or the arm unit has intruded into the intrusion allowed region, the action instruction unit issues an instruction to output a warning.

(10)

The control device according to any one of (1) to (9), in which the non-contact operation with respect to the arm unit by the user includes a hands-free operation by the user operating the arm unit without using his or her hands, and the hands-free operation includes an operation via at least any of a voice, a line of sight, a head track, a gesture, or a foot switch.

(11)

The control device according to any one of (1) to (9), in which a non-contact operation with respect to the arm unit by the user includes an operation of the arm unit in a master-slave scheme.

(12)

The control device according to any one of (1) to (11), in which the medical instrument is an electronic imaging microscope unit that enlarges and photographs an observation target.

(13)

A control method including:

setting, by a processor, an intrusion appropriateness region for which appropriateness of intrusion of a medical instrument or an arm unit supporting the medical instrument is determined in a space on a basis of a peripheral image showing a peripheral state of the medical instrument or the arm unit;

determining presence/absence of intrusion of the medical instrument or the arm unit into the intrusion appropriateness region when driving of the arm unit is controlled in accordance with a non-contact operation by a user with respect to the arm unit; and causing an intrusion hindering action for hindering intrusion of the medical instrument or the arm unit into the intrusion appropriateness region to be executed in accordance with a determination result of the presence/absence of intrusion of the medical instrument or the arm unit into the intrusion appropriateness region.

(14)

A surgical system including:

a microscope unit configured to be supported by an arm unit and to enlarge and photograph an operating site;

a display device configured to display an image of the operating site photographed by the microscope unit;

a peripheral image acquisition camera configured to photograph a peripheral image showing a peripheral state of the microscope unit or the arm unit;

a driving control unit configured to control driving of the arm unit;

a region setting unit configured to set an intrusion appropriateness region for which appropriateness of intrusion of the microscope unit or the arm unit is determined in a space on a basis of the peripheral image photographed by the peripheral image acquisition camera;

an intrusion determination unit configured to determine presence/absence of intrusion of the microscope unit or the arm unit into the intrusion appropriateness region when the driving control unit controls driving of the arm unit in accordance with a non-contact operation by a user with respect to the arm unit; and an action instruction unit configured to cause an intrusion hindering action for hindering intrusion of the microscope unit or the arm unit into the intrusion appropriateness region to be executed in accordance with a determination result of the intrusion determination unit.

REFERENCE SIGNS LIST 10, 10a surgical system
110 observation device
120, 120a display device
130 peripheral image acquisition camera
140, 140a control device
141 image processing unit
142 region setting unit
143 operation mode setting unit
144 intrusion determination unit
145 action instruction unit
146 driving control unit
147 warning control unit
150 hands-free input device
151 microphone
152 eyeglass-type wearable device
153 foot switch
154 operation recognition camera
155 marker
160 operation recognition unit
161 voice recognition unit
162 line-of-sight recognition unit
163 head track recognition unit
164 gesture recognition unit
165 foot switch operation recognition unit
170 manual input device
180 warning output unit

What is claimed is:

1. A control device comprising:
circuitry configured to control driving of an arm that supports a medical instrument;
set an intrusion appropriateness region for which appropriateness of intrusion of the medical instrument or the arm is determined in a space on a basis of a peripheral image showing a peripheral state of the medical instrument or the arm;
determine presence/absence of intrusion of the medical instrument or the arm into the intrusion appropriateness region when driving the arm is controlled in accordance with a non-contact operation by a user with respect to the arm; and cause an intrusion hindering action for hindering intrusion of the medical instrument or the arm into the intrusion appropriateness region to be executed in accordance with a determination result.

2. The control device according to claim 1, wherein the intrusion hindering action is at least any of an operation of the arm to avoid intrusion into the intrusion appropriateness region or output of a warning.

3. The control device according to claim 1, wherein the intrusion appropriateness region includes at least any of an intrusion prohibited region that is a region into which the medical instrument or the arm is prohibited from intruding within a movable range of the arm, an intrusion attention region that is a region into which the medical instrument or the arm is allowed to partially intrude within the movable range of the arm, or an intrusion allowed region that is a region into which the medical instrument or the arm is allowed to intrude within the movable range of the arm.

4. The control device according to claim 3, wherein the peripheral image includes a state inside an operating room, and the intrusion prohibited region includes a region in which at least any of a patient or a surgical apparatus near a patient bed is present.

5. The control device according to claim 3, wherein the peripheral image includes a state inside an operating room, and the intrusion attention region includes a region in which at least any of a cable suspended in the operating room or a cloth suspended in the operating room is present.

6. The control device according to claim 3, wherein the peripheral image includes a state inside an operating room, and the intrusion allowed region includes a region in which medical staff is present.

7. The control device according to claim 3, wherein, on condition that the circuitry determines that the medical instrument or the arm intruded into the intrusion prohibited region, the circuitry is configured to issue an instruction to stop an operation of the arm and an instruction to output a warning.

8. The control device according to claim 3, wherein the arm is configured to have a redundant degree of freedom with respect to movement of the medical instrument, and
on condition that the circuitry determines that the medical instrument or the arm intruded into the intrusion attention region, the circuitry is configured to issue an instruction to cause the arm to operate such that the arm does not intrude into the intrusion attention region while a position and an attitude of the medical instrument are maintained and an instruction to output a warning.

9. The control device according to claim 3, wherein, on condition that the circuitry determines that the medical instrument or the arm has intruded into the intrusion allowed region, the circuitry is configured to issue an instruction to output a warning.

10. The control device according to claim 1, wherein the non-contact operation with respect to the arm by the user includes a hands-free operation by the user operating the arm without using his or her hands, and the hands-free operation includes an operation via at least any of a voice, a line of sight, a head track, a gesture, or a foot switch.

11. The control device according to claim 1, wherein a non-contact operation with respect to the arm by the user includes an operation of the arm in a master-slave scheme.

12. The control device according to claim 1, wherein the medical instrument is an electronic imaging microscope that enlarges and photographs an observation target.

13. A control method comprising:
setting, by a processor, an intrusion appropriateness region for which appropriateness of intrusion of a medical instrument or an arm supporting the medical instrument is determined in a space on a basis of a peripheral image showing a peripheral state of the medical instrument or the arm;
determining presence/absence of intrusion of the medical instrument or the arm into the intrusion appropriateness region when driving of the arm is controlled in accordance with a non-contact operation by a user with respect to the arm; and
causing an intrusion hindering action for hindering intrusion of the medical instrument or the arm into the intrusion appropriateness region to be executed in accordance with a determination result of the presence/absence of intrusion of the medical instrument or the arm into the intrusion appropriateness region.

14. A surgical system comprising:
a medical instrument configured to be supported by an arm and to enlarge and photograph an operating site;
a display configured to display an image of the operating site photographed by the medical instrument;
a peripheral image acquisition camera configured to photograph a peripheral image showing a peripheral state of the medical instrument or the arm; and
circuitry configured to:
control driving of the arm;
set an intrusion appropriateness region for which appropriateness of intrusion of the medical instrument or the arm is determined in a space on a basis of the peripheral image photographed by the peripheral image acquisition camera;
determine presence/absence of intrusion of the medical instrument or the arm into the intrusion appropriateness region when driving the arm in accordance with a non-contact operation by a user with respect to the arm; and
cause an intrusion hindering action for hindering intrusion of the medical instrument or the arm into the intrusion appropriateness region to be executed in accordance with a determination result.

15. The surgical system according to claim 14, wherein the intrusion appropriateness region includes at least any of an intrusion prohibited region that is a region into which the medical instrument or the arm is prohibited from intruding within a movable range of the arm, an intrusion attention region that is a region into which the medical instrument or the arm is allowed to partially intrude within the movable range of the arm, or an intrusion allowed region that is a region into which the medical instrument or the ann is allowed to intrude within the movable range of the aim.

16. The surgical system according to claim 14,
wherein the medical instrument is an electronic imaging microscope that enlarges and photographs an observation target.

17. The control method according to claim 13,
wherein the intrusion appropriateness region includes at least any of an intrusion prohibited region that is a region into which the medical instrument or the arm is prohibited from intruding within a movable range of the arm, an intrusion attention region that is a region into which the medical instrument or the arm is allowed to partially intrude within the movable range of the arm, or an intrusion allowed region that is a region into which the medical instrument or the arm is allowed to intrude within the movable range of the arm.

* * * * *